(12) United States Patent
Katsanis et al.

(10) Patent No.: US 8,163,482 B2
(45) Date of Patent: Apr. 24, 2012

(54) BBS10 RELATED DIAGNOSTIC METHODS FOR BARDET-BIEDL SYNDROME

(76) Inventors: Nicholas Katsanis, Perry Hall, MD (US); Helene Dollfus, Strasbourg (FR); Corinne Stoetzel, Segersheim (FR); Erica E. Davis, Parkville, MD (US); Philip L. Beales, London (GB); Jean-Louis Mandel, Schiltigheim (FR); Richard Alan Lewis, Houston, TX (US)

( * ) Notice: Subject to any disclaimer, the term of this patent is extended or adjusted under 35 U.S.C. 154(b) by 124 days.

(21) Appl. No.: 12/280,498

(22) PCT Filed: Feb. 23, 2007

(86) PCT No.: PCT/US2007/062669
§ 371 (c)(1),
(2), (4) Date: Feb. 2, 2010

(87) PCT Pub. No.: WO2007/101094
PCT Pub. Date: Sep. 7, 2007

(65) Prior Publication Data
US 2010/0130429 A1    May 27, 2010

Related U.S. Application Data

(60) Provisional application No. 60/776,188, filed on Feb. 23, 2006.

(51) Int. Cl.
*C12Q 1/68* (2006.01)
(52) U.S. Cl. .................................. 435/6.1; 435/6.11
(58) Field of Classification Search .................. None
See application file for complete search history.

(56) References Cited

FOREIGN PATENT DOCUMENTS

| WO | WO 01/36440 | * | 5/2001 |
|----|----|----|----|
| WO | WO-03/040369 A2 | | 5/2003 |
| WO | WO-03/093427 A2 | | 11/2003 |
| WO | WO-03/102141 A2 | | 12/2003 |
| WO | WO-2004/048511 A2 | | 6/2004 |
| WO | WO-2005/113812 A2 | | 12/2005 |
| WO | WO-2008/016356 A2 | | 2/2008 |

OTHER PUBLICATIONS

Badano, J.L. et al., "Heterozygous Mutations in BBS1, BBS2 and BBS6 Have a Potential Epistatic Effect on Bardet-Biedl Patients with Two Mutations at a Second BBS locu," Human Molecular Genetics, 12(14):1651-1659 (2003).
Katsanis, N. et al., "Exploring the Molecular Basis of Bardet-Biedl Syndrome," Human Molecular Genetics, 10(20):2293-2299 (2001).
White, D.R.A. et al., "Autozygosity Mapping of Bardet-Biedl Syndrome to 12q21.2 and Confirmation of FLJ23560 as BBS10," Euro. J. of Human Genetics, 15(2):173-178 (2007).
Dollfus, H. et al., "Bardet-Biedl Syndrome: A Unique Family for a Major Gene (BBS10)," M/S Medecine Sciences, 22(11):901-904 (2006).
Laurier, V. et al., "Pitfalls of Homozygosity Mapping: An Extended Consanguineous Bardet-Biedl Syndrome Family with Two Mutuant Genes (BBS2, BBS10), Three Mutations, But No Triallelism," Euro. J. of Human Genetics, 14(11):1195-1203 (2006).
Supplementary European Search Report for EP 07 75 7393 dated Jun. 2, 2009.

* cited by examiner

*Primary Examiner* — Prema Mertz
(74) *Attorney, Agent, or Firm* — Foley Hoag LLP

(57) ABSTRACT

The present invention relates to the identification of a gene, designated BBS1O, that is involved in the genetic disease Bardet Biedl Syndrome (BBS), which is characterized by such diverse symptoms as obesity, diabetes, hypertension, mental retardation, renal cancer and other abnormalities, retinopathy and hypogonadism. Methods of use for the gene, for example in diagnosis and therapy of BBS, also are described.

6 Claims, 14 Drawing Sheets

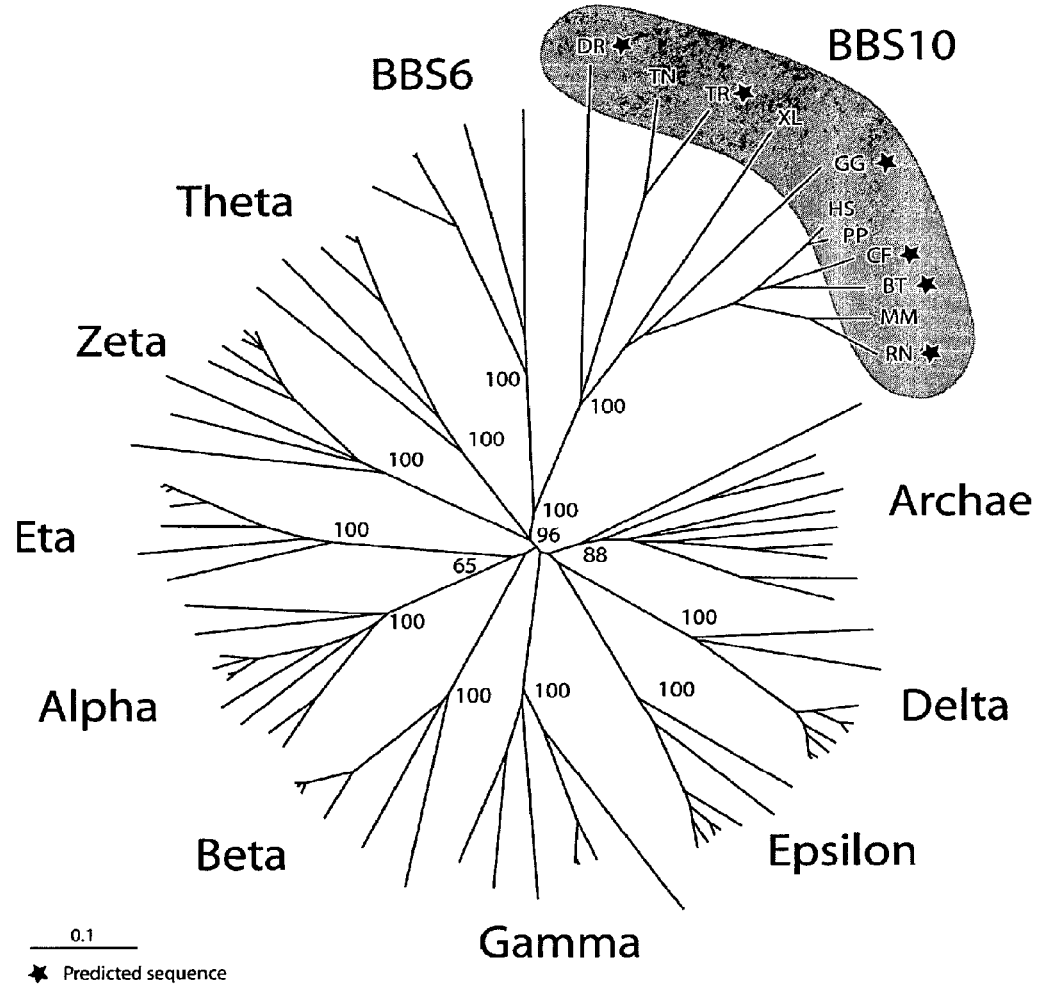

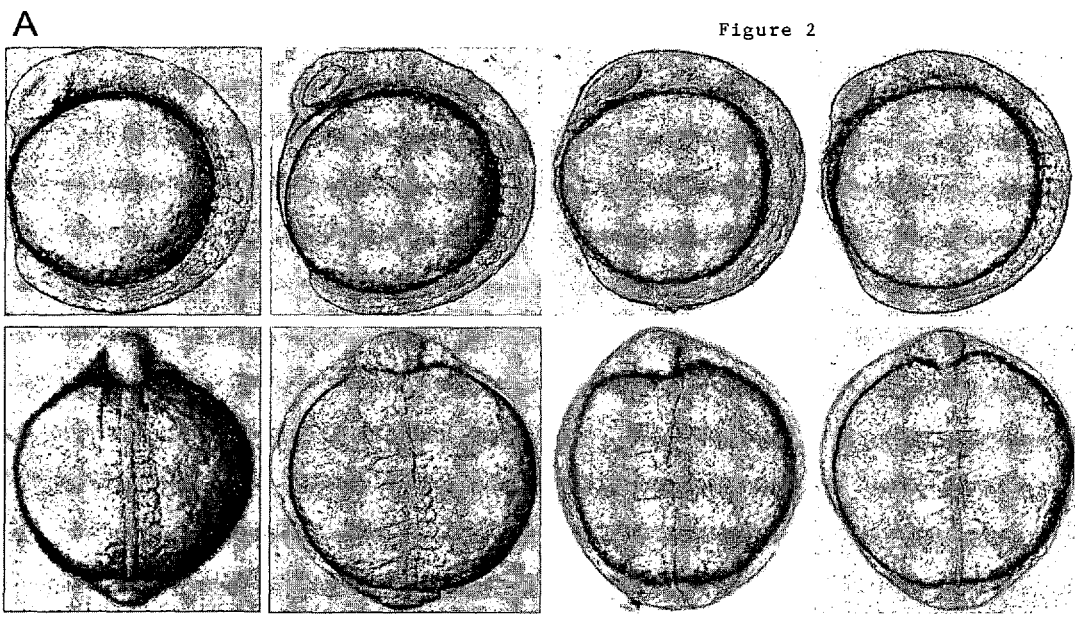
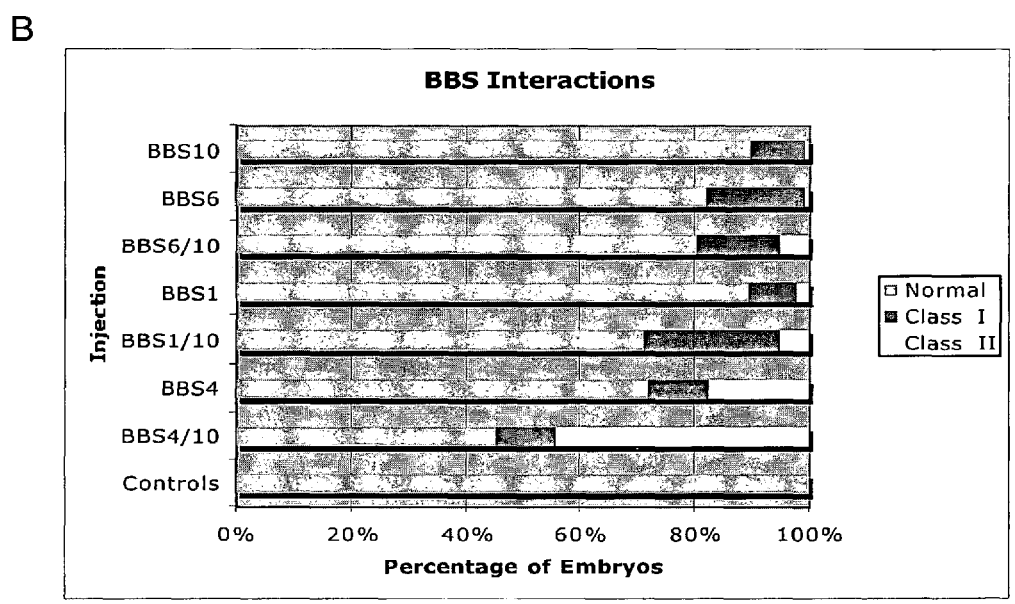
Figure 2

Figure 3

BBS10- Long open reading frame

```
  1    M   L   S   S   M   A   A   A   G   S   V   K   A   A   L   Q   V   A   E   V
  1    ATGTTAAGTTCTATGGCCGCTGCAGGGTCTGTGAAGGCGGCGTTGCAGGTGGCCGAGGTG

21    L   E   A   I   V   S   C   C   V   G   P   E   G   R   Q   V   L   C   T   K
 61    CTGGAAGCCATCGTGAGCTGCTGCGTGGGGCCCGAGGGACGGCAAGTTTTGTGTACGAAG

41    P   T   G   E   V   L   L   S   R   N   G   G   R   L   L   E   A   L   H   L
121    CCCACTGGCGAGGTGCTTCTCAGCCGGAATGGAGGCCGCCTCCTGGAGGCGCTACACTTA

61    E   H   P   I   A   R   M   I   V   D   C   V   S   S   H   L   K   K   T   G
181    GAGCATCCCATAGCCAGGATGATAGTGGACTGTGTTTCCAGTCATCTCAAAAAAACAGGA

81    D   G   A   K   T   F   I   I   F   L   C   H   L   L   R   G   L   H   A   I
241    GATGGTGCAAAAACATTTATTATCTTTCTTTGCCATTTGCTTAGAGGACTTCATGCAATC

101    T   D   R   E   K   D   P   L   M   C   E   N   I   Q   T   H   G   R   H   W
301    ACAGACAGAGAAAAGGATCCTTTGATGTGTGAAAACATTCAAACCCATGGAAGGCATTGG

121    K   N   C   S   R   W   K   F   I   S   Q   A   L   L   T   F   Q   T   Q   I
361    AAAAATTGTTCTCGGTGGAAATTTATTTCCCAGGCTCTCCTAACGTTTCAGACACAAATA

141    L   D   G   I   M   D   Q   Y   L   S   R   H   F   L   S   I   F   S   S   A
421    TTAGACGGTATTATGGACCAGTACCTAAGTAGACACTTTTTGTCTATCTTTTCGTCTGCT

161    K   E   R   T   L   C   R   S   S   L   E   L   L   L   E   A   Y   F   C   G
481    AAAGAGAGAACATTGTGTAGGAGCTCTTTAGAGTTGCTCTTAGAAGCATACTTTTGTGGA

181    R   V   G   R   N   N   H   K   F   I   S   Q   L   M   C   D   Y   F   F   K
541    AGAGTGGGAAGAAATAATCATAAATTTATTTCACAGTTGATGTGTGACTACTTTTTCAAG

201    C   M   T   C   K   S   G   I   G   V   F   E   L   V   D   D   H   F   V   E
601    TGTATGACTTGTAAAAGTGGGATTGGTGTATTTGAGTTAGTGGATGACCATTTTGTAGAG

221    L   N   V   G   V   T   G   L   P   V   S   D   S   R   I   I   A   G   L   V
661    TTGAATGTTGGTGTCACTGGCCTTCCTGTTTCAGATTCCAGGATCATAGCTGGTCTTGTG

241    L   Q   K   D   F   S   V   Y   R   P   A   D   G   D   M   R   M   V   I   V
721    CTTCAGAAAGATTTTTCTGTGTACCGCCCAGCAGATGGTGACATGCGAATGGTGATAGTA

261    T   E   T   I   Q   P   L   F   S   T   S   G   S   E   F   I   L   N   S   E
781    ACAGAAACCATTCAGCCTCTTTTTTCCACTTCTGGATCAGAGTTTATTCTAAATTCAGAA

281    A   Q   F   Q   T   S   Q   F   W   I   M   E   K   T   K   A   I   M   K   H
841    GCACAGTTTCAGACATCTCAATTTTGGATTATGGAAAAGACAAAAGCAATAATGAAACAT

301    L   H   S   Q   N   V   K   L   L   I   S   S   V   K   Q   P   D   L   V   S
901    CTACATAGTCAGAATGTAAAATTGCTCATATCTAGTGTGAAACAACCAGATTTAGTTAGT

321    Y   Y   A   G   V   N   G   I   S   V   V   E   C   L   S   S   E   E   V   S
961    TATTATGCAGGGGTGAATGGCATATCAGTGGTTGAGTGTTTATCATCAGAAGAAGTTTCT

341    L   I   R   R   I   I   G   L   S   P   F   V   P   P   Q   A   F   S   Q   C
1021   CTTATCCGGAGGATCATTGGTCTTTCTCCATTTGTACCACCACAGGCCTTTTCGCAGTGT
```

Figure 3 (cont.)

```
 361    E  I  P  N  T  A  L  V  K  F  C  K  P  L  I  L  R  S  K  R
1081    GAAATACCTAACACTGCTTTGGTGAAATTTTGTAAACCTCTTATCCTTAGATCCAAAAGA

381    Y  V  H  L  G  L  I  S  T  C  A  F  I  P  H  S  I  V  L  C
1141    TATGTTCATCTAGGCTTGATAAGCACATGTGCATTTATACCACACTCTATAGTTCTTTGT

401    G  P  V  H  G  L  I  E  Q  H  E  D  A  L  H  G  A  L  K  M
1201    GGACCAGTGCATGGTCTCATTGAACAACATGAGGATGCTTTACATGGAGCACTTAAAATG

421    L  R  Q  L  F  K  D  L  D  L  N  Y  M  T  Q  T  N  D  Q  N
1261    CTTCGGCAATTATTTAAAGACCTTGATCTAAATTACATGACACAAACCAATGACCAAAAT

441    G  T  S  S  L  F  I  Y  K  N  S  G  E  S  Y  Q  A  P  D  P
1321    GGCACTTCAAGTCTTTTTATTTATAAGAACAGTGGAGAAAGTTATCAAGCACCAGATCCT

461    G  N  G  S  I  Q  R  P  Y  Q  D  T  V  A  E  N  K  D  A  L
1381    GGTAATGGCTCAATACAAAGGCCTTATCAGGACACAGTTGCAGAGAACAAAGATGCATTG

481    E  K  T  Q  T  Y  L  K  V  H  S  N  L  V  I  P  D  V  E  L
1441    GAAAAAACTCAAACATATTTAAAAGTACATTCTAATTTGGTAATTCCAGATGTAGAATTA

501    E  T  Y  I  P  Y  S  T  P  T  L  T  P  T  D  F  Q  T  V
1501    GAAACATATATTCCGTATTCAACCCCCACACTGACACCAACAGATACATTCCAAACAGTT

521    E  T  L  T  C  L  S  L  E  R  N  R  L  T  D  Y  Y  E  P  L
1561    GAAACGCTGACATGTTTGTCTTTGGAAAGAAACAGGCTAACTGATTATTATGAACCATTA

541    L  K  N  N  S  T  A  Y  S  T  R  G  N  R  I  E  I  S  Y  E
1621    CTCAAGAACAATTCCACTGCTTATTCAACAAGGGGAAATAGAATAGAAATTTCTTACGAA

561    N  L  Q  V  T  N  I  T  R  K  G  S  M  L  P  V  S  C  K  L
1681    AATTTACAGGTCACAAATATTACTAGAAAGGGAAGCATGTTACCAGTGAGCTGTAAGTTA

581    P  N  M  G  T  S  Q  S  Y  L  S  S  S  M  P  A  G  C  V  L
1741    CCGAATATGGGTACTTCCCAGAGTTACCTTTCCTCATCTATGCCAGCTGGTTGTGTTTTG

601    P  V  G  G  N  F  E  I  L  L  H  Y  Y  L  L  N  Y  A  K  K
1801    CCAGTAGGTGGTAATTTTGAGATCTTGTTACATTACTATCTTCTCAATTATGCCAAAAAA

621    C  H  Q  S  E  E  T  M  V  S  M  I  I  A  N  A  L  L  G  I
1861    TGCCATCAATCAGAAGAAACCATGGTTAGTATGATAATAGCTAATGCACTTTTAGGCATT

641    P  K  V  L  Y  K  S  K  T  G  K  Y  S  F  P  H  T  Y  I  R
1921    CCCAAAGTCCTTTATAAATCTAAAACAGGAAAGTACAGCTTTCCACATACATATATAAGA

661    A  V  H  A  L  Q  T  N  Q  P  L  V  S  S  Q  T  G  L  E  S
1981    GCTGTCCATGCACTGCAAACCAATCAACCCTTGGTAAGCAGTCAGACAGGTTTGGAATCA

681    V  M  G  K  Y  Q  L  L  T  S  V  L  Q  C  L  T  K  I  L  T
2041    GTAATGGGTAAATACCAGCTACTAACTTCAGTTCTTCAGTGTTTGACAAAAATATTAACC

701    I  D  M  V  I  T  V  K  R  H  P  Q  K  V  H  N  Q  D  S  E
2101    ATTGACATGGTAATCACTGTTAAGAGACACCCTCAGAAAGTTCACAATCAAGATTCAGAA

721    D  E  L  -
2161    GATGAACTATAA
```

Figure 4

BBS10- Short open reading frame

```
  1    M   I   V   D   C   V   S   S   H   L   K   K   T   G   D   G   A   K   T   F
  1    ATGATAGTGGACTGTGTTTCCAGTCATCTCAAAAAAACAGGAGATGGTGCAAAAACATTT

21    I   I   F   L   C   H   L   L   R   G   L   H   A   I   T   D   R   E   K   D
 61    ATTATCTTTCTTTGCCATTTGCTTAGAGGACTTCATGCAATCACAGACAGAGAAAAGGAT

41    P   L   M   C   E   N   I   Q   T   H   G   R   H   W   K   N   C   S   R   W
121    CCTTTGATGTGTGAAAACATTCAAACCCATGGAAGGCATTGGAAAAATTGTTCTCGGTGG

61    K   F   I   S   Q   A   L   L   T   F   Q   T   Q   I   L   D   G   I   M   D
181    AAATTTATTTCCCAGGCTCTCCTAACGTTTCAGACACAAATATTAGACGGTATTATGGAC

81    Q   Y   L   S   R   H   F   L   S   I   F   S   S   A   K   E   R   T   L   C
241    CAGTACCTAAGTAGACACTTTTTGTCTATCTTTTCGTCTGCTAAAGAGAGAACATTGTGT

101    R   S   S   L   E   L   L   L   E   A   Y   F   C   G   R   V   G   R   N   N
301    AGGAGCTCTTTAGAGTTGCTCTTAGAAGCATACTTTTGTGGAAGAGTGGGAAGAAATAAT

121    H   K   F   I   S   Q   L   M   C   D   Y   F   F   K   C   M   T   C   K   S
361    CATAAATTTATTTCACAGTTGATGTGTGACTACTTTTTCAAGTGTATGACTTGTAAAAGT

141    G   I   G   V   F   E   L   V   D   D   H   F   V   E   L   N   V   G   V   T
421    GGGATTGGTGTATTTGAGTTAGTGGATGACCATTTTGTAGAGTTGAATGTTGGTGTCACT

161    G   L   P   V   S   D   S   R   I   I   A   G   L   V   L   Q   K   D   F   S
481    GGCCTTCCTGTTTCAGATTCCAGGATCATAGCTGGTCTTGTGCTTCAGAAAGATTTTTCT

181    V   Y   R   P   A   D   G   D   M   R   M   V   I   V   T   E   T   I   Q   P
541    GTGTACCGCCCAGCAGATGGTGACATGCGAATGGTGATAGTAACAGAAACCATTCAGCCT

201    L   F   S   T   S   G   S   E   F   I   L   N   S   E   A   Q   F   Q   T   S
601    CTTTTTTCCACTTCTGGATCAGAGTTTATTCTAAATTCAGAAGCACAGTTTCAGACATCT

221    Q   F   W   I   M   E   K   T   K   A   I   M   K   H   L   H   S   Q   N   V
661    CAATTTTGGATTATGGAAAAGACAAAAGCAATAATGAAACATCTACATAGTCAGAATGTA

241    K   L   L   I   S   S   V   K   Q   P   D   L   V   S   Y   Y   A   G   V   N
721    AAATTGCTCATATCTAGTGTGAAACAACCAGATTTAGTTAGTTATTATGCAGGGGTGAAT

261    G   I   S   V   V   E   C   L   S   S   E   E   V   S   L   I   R   R   I   I
781    GGCATATCAGTGGTTGAGTGTTTATCATCAGAAGAAGTTTCTCTTATCCGGAGGATCATT

281    G   L   S   P   F   V   P   P   Q   A   F   S   Q   C   E   I   P   N   T   A
841    GGTCTTTCTCCATTTGTACCACCACAGGCCTTTTCGCAGTGTGAAATACCTAACACTGCT

301    L   V   K   F   C   K   P   L   I   L   R   S   K   R   Y   V   H   L   G   L
901    TTGGTGAAATTTTGTAAACCTCTTATCCTTAGATCCAAAAGATATGTTCATCTAGGCTTG

321    I   S   T   C   A   F   I   P   H   S   I   V   L   C   G   P   V   H   G   L
961    ATAAGCACATGTGCATTTATACCACACTCTATAGTTCTTTGTGGACCAGTGCATGGTCTC

341    I   E   Q   H   E   D   A   L   H   G   A   L   K   M   L   R   Q   L   F   K
1021   ATTGAACAACATGAGGATGCTTTACATGGAGCACTTAAAATGCTTCGGCAATTATTTAAA
```

Figure 4 (cont.)

```
361   D   L   D   L   N   Y   M   T   Q   T   N   D   Q   N   G   T   S   S   L   F
1081  GACCTTGATCTAAATTACATGACACAAACCAATGACCAAAATGGCACTTCAAGTCTTTTT

381   I   Y   K   N   S   G   E   S   Y   Q   A   P   D   P   G   N   G   S   I   Q
1141  ATTTATAAGAACAGTGGAGAAAGTTATCAAGCACCAGATCCTGGTAATGGCTCAATACAA

401   R   P   Y   Q   D   T   V   A   E   N   K   D   A   L   E   K   T   Q   T   Y
1201  AGGCCTTATCAGGACACAGTTGCAGAGAACAAAGATGCATTGGAAAAAACTCAAACATAT

421   L   K   V   H   S   N   L   V   I   P   D   V   E   L   E   T   Y   I   P   Y
1261  TTAAAAGTACATTCTAATTTGGTAATTCCAGATGTAGAATTAGAAACATATATTCCGTAT

441   S   T   P   T   L   T   P   T   D   T   F   Q   T   V   E   T   L   T   C   L
1321  TCAACCCCCACACTGACACCAACAGATACATTCCAAACAGTTGAAACGCTGACATGTTTG

461   S   L   E   R   N   R   L   T   D   Y   Y   E   P   L   L   K   N   N   S   T
1381  TCTTTGGAAAGAAACAGGCTAACTGATTATTATGAACCATTACTCAAGAACAATTCCACT

481   A   Y   S   T   R   G   N   R   I   E   I   S   Y   E   N   L   Q   V   T   N
1441  GCTTATTCAACAAGGGGAAATAGAATAGAAATTTCTTACGAAAATTTACAGGTCACAAAT

501   I   T   R   K   G   S   M   L   P   V   S   C   K   L   P   N   M   G   T   S
1501  ATTACTAGAAAGGGAAGCATGTTACCAGTGAGCTGTAAGTTACCGAATATGGGTACTTCC

521   Q   S   Y   L   S   S   M   P   A   G   C   V   L   P   V   G   N   F
1561  CAGAGTTACCTTTCCTCATCTATGCCAGCTGGTTGTGTTTTGCCAGTAGGTGGTAATTTT

541   E   I   L   L   H   Y   Y   L   L   N   Y   A   K   K   C   H   Q   S   E   E
1621  GAGATCTTGTTACATTACTATCTTCTCAATTATGCCAAAAAATGCCATCAATCAGAAGAA

561   T   M   V   S   M   I   I   A   N   A   L   L   G   I   P   K   V   L   Y   K
1681  ACCATGGTTAGTATGATAATAGCTAATGCACTTTTAGGCATTCCCAAAGTCCTTTATAAA

581   S   K   T   G   K   Y   S   F   P   H   T   Y   I   R   A   V   H   A   L   Q
1741  TCTAAAACAGGAAAGTACAGCTTTCCACATACATATATAAGAGCTGTCCATGCACTGCAA

601   T   N   Q   P   L   V   S   S   Q   T   G   L   E   S   V   M   G   K   Y   Q
1801  ACCAATCAACCCTTGGTAAGCAGTCAGACAGGTTTGGAATCAGTAATGGGTAAATACCAG

621   L   L   T   S   V   L   Q   C   L   T   K   I   L   T   I   D   M   V   I   T
1861  CTACTAACTTCAGTTCTTCAGTGTTTGACAAAAATATTAACCATTGACATGGTAATCACT

641   V   K   R   H   P   Q   K   V   H   N   Q   D   S   E   D   E   L   -
1921  GTTAAGAGACACCCTCAGAAAGTTCACAATCAAGATTCAGAAGATGAACTATAA
```

Figure 5

| Mutated Allele 1 | Mutated Allele 2 | BBS families* | Ethnic Origin | Mutated or variant allele 3 (other BBS genes) |
|---|---|---|---|---|
| A13fsX81 | K243fsX258 | AR92-05 | Caucasian | |
| R34P | C91fsX95 | I.25 | Caucasian | BBS6: I339V # |
| R49W | R49W | V.7 | Turkish | |
| R49W | V707fsX708 | AR381-03 | Caucasian | |
| R49W | L414S | V.17 | Caucasian | |
| R49W | C91fsX95 | AR77-04 | Caucasian | |
| S73fsX91 | S73fsX91 | IV.14 | Lebanese | |
| C91W | A474fsX483 | AR751-03 | Caucasian | |
| C91fsX95 | C91fsX95 | 18 families ** | Caucasians, Afghani, Gypsy Turkish | BBS6: R517C (PB159.1) |
| C91fsX95 | C91W | VI.11; VII.21 | Caucasians | BBS1:M390R(VI.11) BBS4:L351R (VII.21) |
| C91fsX95 | C195W | I.17; AR853-03 | Caucasian | BBS6: T237A (I.17) # |
| C91fsX95 | Y197C | AR94-03 | Caucasian | |
| C91fsX95 | F199del | AR769-02 | Caucasian | BBS6 : A242S # |
| C91fsX95 | V230fsX236 | AR365-03 | Caucasian | |
| C91fsX95 | S303fsX305 | AR42; AR708-03; II.4 | Caucasians | BBS4 : N165H (AR708-03) |
| C91fsX95 | Y321X | V.29 | Caucasian | |
| C91fsX95 | S329L/P363L | AR199-03 | Caucasian | BBS1: L544H |
| C91fsX95 | L348fsX360 | III.21 | Caucasian | |
| C91fsX95 | L414S | AR286-04 | Caucasian | |
| C91fsX95 | Y613C | AR849-03 | Caucasian | |
| L170S | L170S | III.13 | Tunisian | |
| V240G | V240G | II.16 | Caucasian | |
| Q242fsX258 | Q242fsX258 | V.27 | Lebanese | |
| K243fsX258 | K243fsX258 | AR287-03 | Caucasian | BBS7: H323R |
| S303fsX305 | G677V | AR433-05 | Caucasian | BBS1: IVS13-2A->G |
| L308F/K57R | L308F/K579R | KK9-04 | Middle Eastern | |
| S311A | S311A | III.8 | Lebanese | |
| L348fsX360 | T689P | V.16 | Caucasian | |
| L367fsX368 | L367fsX368 | AR300-04 | Caucasian | |
| L414S | L414S | PB70.1 | Caucasian | |
| T483fsX490 | T483fsX490 | VI.7 | Caucasian | |
| T514fsX523 | T514fsX523 | VII.13 | Portugal | |
| C91fsX95 | | 5 families *** | Caucasians | |
| Q242fsX258 | | KF01-05 | Middle Eastern | |
| V230fsX236 | | AR618-04 | Caucasian | |
| F275fsX281 | | KK15-03 | Middle Eastern | |
| S303fsX305 | | AR709-03 | | BBS1: M390R/ E549X |
| Y559fsX576 | | AR232-03 | Caucasian | |
| Y613H | | VI.23 | Caucasian | |
| V707fsX708 | | AR246-03 | Caucasian | BBS1: M390R |

Figure 6

| Gene | Exon/Intron | Nucleotide change | Predicted effect | Allele frequency in 125 BBS families | Alleles frequency in 96 french controls |
|---|---|---|---|---|---|
| BBS10 | | 1-52C>T | | 3,20% | 0,00% |
| | exon 2 | 424G>A | D142N | 0,90% | 2,00% |
| | exon 2 | 1616C>T | P539L | 7,50% | 13,50% |
| | exon 2 | 1631A>G | N544S | 1,40% | 2,08% |

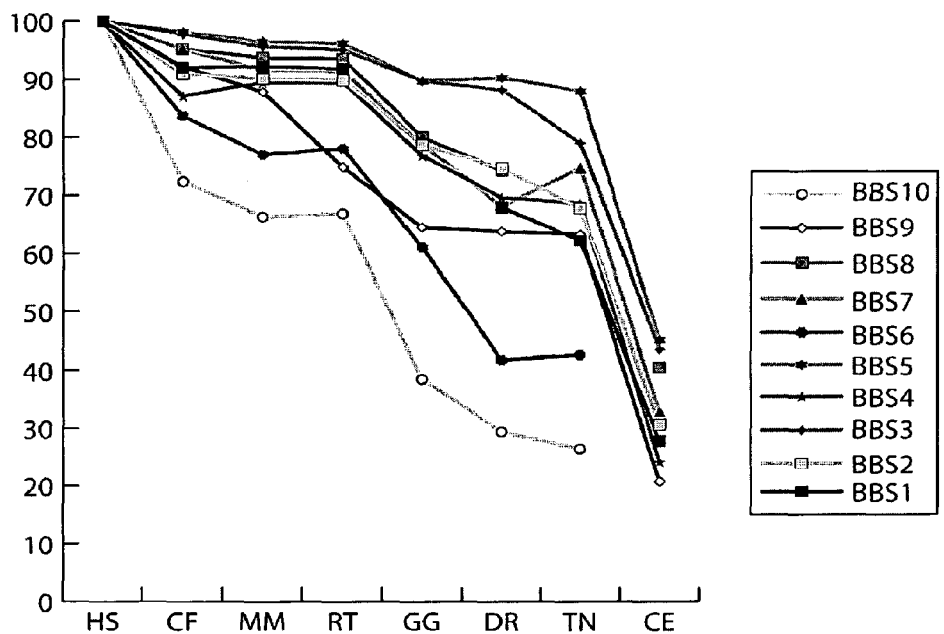
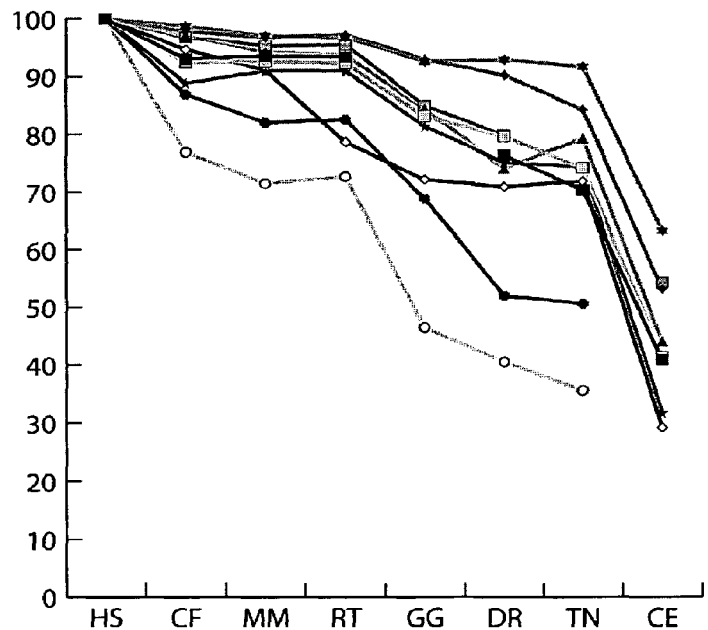
Figure 8

Figure 9

| BBS10 | | | | |
|---|---|---|---|---|
| mutations | nucletide change | exon | Nombre alleles/famille | Familles ( )=nb allele/famille |
| V11G | c.32T>G | 1 | 2 | III.8 |
| R34P | c.101G>C | 1 | 1 | I.25 |
| G43D | c.128G>A | 1 | 1 | VII.28 |
| R49W | c.145C>T | 1 | 5 | V.7(2) ; AR 381-03(1), V.17(1); AR 77-04(1) |
| C91W | c.273C>G | 2 | 3 | AR 751-03 ; VI.11; VII.21 |
| L170S | c.509T>C | 2 | 2 | III.13 |
| C195W | c.585T>G | 2 | 2 | I.17; AR 853-03 |
| Y197C | c.590A>G | 2 | 1 | AR94-03 |
| V240G | c.719T>G | 2 | 2 | II.16 |
| L308F | c.924G>T | 2 | 2 | KK 9-04 |
| S311A | c.931T>G | 2 | 2 | III.8 |
| Y321X | c.963T>G | 2 | 1 | V.29 |
| S329L | c.986C>T | 2 | 1 | AR 199-03 |
| P363L | c.1088C>T | 2 | 1 | AR 199-04 |
| L414S | c.1241T>C | 2 | 4 | V.17(1); AR 286-04(1); PB 70.1(2) |
| K579R | c.1736A>G | 2 | 2 | KK 9-04 |
| Y613C | c.1838A>G | 2 | 1 | AR 849-03 |
| Y613H | c.1837T>C | 2 | 1 | VI.23 |
| G677V | c.2030G>T | 2 | 1 | AR 433-05 |
| T689P | c.2065A>C | 2 | 1 | V.16 |
| A13fsX | c.37del GCGGCGTT | 2 | 1 | AR 92-05 |
| S73fsX | c.219del CAGTCATCTCA | 2 | 2 | IV.14 |
| C91fsX | c.271ins T | 2 | 58 | 18 familles HMZ+22 HTZ |
| V230fsX | c.687del T | 2 | 2 | AR 365-03; AR 618-04 |
| Q242fsX | c.724del C | 2 | 3 | V.27(2); KF 01-05(1) |
| K243fsX | c.728del AAGA | 2 | 3 | AR 92-05(1); AR 287-03(2) |
| F275fsX | c.821ins GGATCAGA | 2 | 1 | KK 15-03 |
| S303fsX | c.909del TCAG | 2 | 5 | AR 42(1); AR 708-03(1); II.4(1); AR 433-05(1); AR 709-03(1) |
| L348fsX | c.1043delTT | 2 | 2 | III.21; V.16 |
| L367fsX | c.1101del GG ins T | 2 | 2 | AR 300-04 |
| A474fsX | c.1420del GCAGAGAACAAAG | 2 | 1 | AR 751-03 |
| T483fsX | c.1448del CTCAA | 2 | 2 | VI.7 |
| T514fsX | c.1542del A | 2 | 2 | VII.13 |
| Y559fsX | c.1677del C | 2 | 1 | AR 232-03 |
| V707fsX | c.2118del TG | 2 | 2 | AR 381-03; AR 246-03 |
| 199del F | c.595del TTT | 2 | 1 | AR 769-02 |
| 308del L | c.922del TTG | | | katsanis |
| 198del F, 199del F | c.591del CTTTTT | 2 | | |
| L533fsX | c.1599del AACT | 2 | | |

Figure 10

| BBS1 | M390R | c.1169T>G |
|------|-------|-----------|
| BBS1 | E549X | c.1645G>T |
| BBS1 |       | IVS13-2A>G |
| BBS1 | L544H | c.1631T>A |
| BBS4 | L351R | c.1052T>G |
| BBS4 | N165H | c.493A>C |
| BBS6 | T237A | c.709A>G |
| BBS6 | A242S | c.724G>T |
| BBS6 | I339V | c.1015A>G |
| BBS6 | R517C | c.1549C>T |
| BBS7 | H323R | c.968A>G |

SEQUENCE LISTING

```
<160> NUMBER OF SEQ ID NOS: 34

<210> SEQ ID NO 1
<211> LENGTH: 2172
<212> TYPE: DNA
<213> ORGANISM: Homo sapiens
<220> FEATURE:
<221> NAME/KEY: CDS
<222> LOCATION: (1)..(2169)

<400> SEQUENCE: 1
```

```
atg tta agt tct atg gcc gct gca ggg tct gtg aag gcg gcg ttg cag    48
Met Leu Ser Ser Met Ala Ala Ala Gly Ser Val Lys Ala Ala Leu Gln
 1               5                  10                  15 gtg gcc gag gtg ctg gaa gcc atc gtg agc tgc tgc gtg ggg ccc gag    96
Val Ala Glu Val Leu Glu Ala Ile Val Ser Cys Cys Val Gly Pro Glu
             20                  25                  30 gga cgg caa gtt ttg tgt acg aag ccc act ggc gag gtg ctt ctc agc   144
Gly Arg Gln Val Leu Cys Thr Lys Pro Thr Gly Glu Val Leu Leu Ser
         35                  40                  45 cgg aat gga ggc cgc ctc ctg gag gcg cta cac tta gag cat ccc ata   192
Arg Asn Gly Gly Arg Leu Leu Glu Ala Leu His Leu Glu His Pro Ile
     50                  55                  60 gcc agg atg ata gtg gac tgt gtt tcc agt cat ctc aaa aaa aca gga   240
Ala Arg Met Ile Val Asp Cys Val Ser Ser His Leu Lys Lys Thr Gly
 65                  70                  75                  80 gat ggt gca aaa aca ttt att atc ttt ctt tgc cat ttg ctt aga gga   288
Asp Gly Ala Lys Thr Phe Ile Ile Phe Leu Cys His Leu Leu Arg Gly
                 85                  90                  95 ctt cat gca atc aca gac aga gaa aag gat cct ttg atg tgt gaa aac   336
Leu His Ala Ile Thr Asp Arg Glu Lys Asp Pro Leu Met Cys Glu Asn
            100                 105                 110 att caa acc cat gga agg cat tgg aaa aat tgt tct cgg tgg aaa ttt   384
Ile Gln Thr His Gly Arg His Trp Lys Asn Cys Ser Arg Trp Lys Phe
        115                 120                 125 att tcc cag gct ctc cta acg ttt cag aca caa ata tta gac ggt att   432
Ile Ser Gln Ala Leu Leu Thr Phe Gln Thr Gln Ile Leu Asp Gly Ile
    130                 135                 140 atg gac cag tac cta agt aga cac ttt ttg tct atc ttt tcg tct gct   480
Met Asp Gln Tyr Leu Ser Arg His Phe Leu Ser Ile Phe Ser Ser Ala
145                 150                 155                 160 aaa gag aga aca ttg tgt agg agc tct tta gag ttg ctc tta gaa gca   528
Lys Glu Arg Thr Leu Cys Arg Ser Ser Leu Glu Leu Leu Leu Glu Ala
                165                 170                 175 tac ttt tgt gga aga gtg gga aga aat aat cat aaa ttt att tca cag   576
Tyr Phe Cys Gly Arg Val Gly Arg Asn Asn His Lys Phe Ile Ser Gln
            180                 185                 190 ttg atg tgt gac tac ttt ttc aag tgt atg act tgt aaa agt ggg att   624
Leu Met Cys Asp Tyr Phe Phe Lys Cys Met Thr Cys Lys Ser Gly Ile
        195                 200                 205 ggt gta ttt gag tta gtg gat gac cat ttt gta gag ttg aat gtt ggt   672
Gly Val Phe Glu Leu Val Asp Asp His Phe Val Glu Leu Asn Val Gly
    210                 215                 220 gtc act ggc ctt cct gtt tca gat tcc agg atc ata gct ggt ctt gtg   720
Val Thr Gly Leu Pro Val Ser Asp Ser Arg Ile Ile Ala Gly Leu Val
225                 230                 235                 240 ctt cag aaa gat ttt tct gtg tac cgc cca gca gat ggt gac atg cga   768
Leu Gln Lys Asp Phe Ser Val Tyr Arg Pro Ala Asp Gly Asp Met Arg
                245                 250                 255 atg gtg ata gta aca gaa acc att cag cct ctt ttt tcc act tct gga   816
Met Val Ile Val Thr Glu Thr Ile Gln Pro Leu Phe Ser Thr Ser Gly
            260                 265                 270 tca gag ttt att cta aat tca gaa gca cag ttt cag aca tct caa ttt   864
Ser Glu Phe Ile Leu Asn Ser Glu Ala Gln Phe Gln Thr Ser Gln Phe
        275                 280                 285 tgg att atg gaa aag aca aaa gca ata atg aaa cat cta cat agt cag   912
Trp Ile Met Glu Lys Thr Lys Ala Ile Met Lys His Leu His Ser Gln
    290                 295                 300 aat gta aaa ttg ctc ata tct agt gtg aaa caa cca gat tta gtt agt   960
Asn Val Lys Leu Leu Ile Ser Ser Val Lys Gln Pro Asp Leu Val Ser
305                 310                 315                 320
```

-continued

| | |
|---|---|
| tat tat gca ggg gtg aat ggc ata tca gtg gtt gag tgt tta tca tca<br>Tyr Tyr Ala Gly Val Asn Gly Ile Ser Val Val Glu Cys Leu Ser Ser<br>325                                  330                         335 | 1008 |
| gaa gaa gtt tct ctt atc cgg agg atc att ggt ctt tct cca ttt gta<br>Glu Glu Val Ser Leu Ile Arg Arg Ile Ile Gly Leu Ser Pro Phe Val<br>        340                        345                       350 | 1056 |
| cca cca cag gcc ttt tcg cag tgt gaa ata cct aac act gct ttg gtg<br>Pro Pro Gln Ala Phe Ser Gln Cys Glu Ile Pro Asn Thr Ala Leu Val<br>355                                  360                         365 | 1104 |
| aaa ttt tgt aaa cct ctt atc ctt aga tcc aaa aga tat gtt cat cta<br>Lys Phe Cys Lys Pro Leu Ile Leu Arg Ser Lys Arg Tyr Val His Leu<br>370                                  375                       380 | 1152 |
| ggc ttg ata agc aca tgt gca ttt ata cca cac tct ata gtt ctt tgt<br>Gly Leu Ile Ser Thr Cys Ala Phe Ile Pro His Ser Ile Val Leu Cys<br>385                              390                       395                   400 | 1200 |
| gga cca gtg cat ggt ctc att gaa caa cat gag gat gct tta cat gga<br>Gly Pro Val His Gly Leu Ile Glu Gln His Glu Asp Ala Leu His Gly<br>                              405                       410                       415 | 1248 |
| gca ctt aaa atg ctt cgg caa tta ttt aaa gac ctt gat cta aat tac<br>Ala Leu Lys Met Leu Arg Gln Leu Phe Lys Asp Leu Asp Leu Asn Tyr<br>                    420                       425                       430 | 1296 |
| atg aca caa acc aat gac caa aat ggc act tca agt ctt ttt att tat<br>Met Thr Gln Thr Asn Asp Gln Asn Gly Thr Ser Ser Leu Phe Ile Tyr<br>435                                  440                       445 | 1344 |
| aag aac agt gga gaa agt tat caa gca cca gat cct ggt aat ggc tca<br>Lys Asn Ser Gly Glu Ser Tyr Gln Ala Pro Asp Pro Gly Asn Gly Ser<br>        450                        455                       460 | 1392 |
| ata caa agg cct tat cag gac aca gtt gca gag aac aaa gat gca ttg<br>Ile Gln Arg Pro Tyr Gln Asp Thr Val Ala Glu Asn Lys Asp Ala Leu<br>465                                  470                       475                   480 | 1440 |
| gaa aaa act caa aca tat tta aaa gta cat tct aat ttg gta att cca<br>Glu Lys Thr Gln Thr Tyr Leu Lys Val His Ser Asn Leu Val Ile Pro<br>                    485                       490                       495 | 1488 |
| gat gta gaa tta gaa aca tat att ccg tat tca acc ccc aca ctg aca<br>Asp Val Glu Leu Glu Thr Tyr Ile Pro Tyr Ser Thr Pro Thr Leu Thr<br>                500                       505                       510 | 1536 |
| cca aca gat aca ttc caa aca gtt gaa acg ctg aca tgt ttg tct ttg<br>Pro Thr Asp Thr Phe Gln Thr Val Glu Thr Leu Thr Cys Leu Ser Leu<br>                    515                       520                       525 | 1584 |
| gaa aga aac agg cta act gat tat tat gaa cca tta ctc aag aac aat<br>Glu Arg Asn Arg Leu Thr Asp Tyr Tyr Glu Pro Leu Leu Lys Asn Asn<br>530                                  535                       540 | 1632 |
| tcc act gct tat tca aca agg gga aat aga ata gaa att tct tac gaa<br>Ser Thr Ala Tyr Ser Thr Arg Gly Asn Arg Ile Glu Ile Ser Tyr Glu<br>545                                  550                       555                   560 | 1680 |
| aat tta cag gtc aca aat att act aga aag gga agc atg tta cca gtg<br>Asn Leu Gln Val Thr Asn Ile Thr Arg Lys Gly Ser Met Leu Pro Val<br>                              565                       570                       575 | 1728 |
| agc tgt aag tta ccg aat atg ggt act tcc cag agt tac ctt tcc tca<br>Ser Cys Lys Leu Pro Asn Met Gly Thr Ser Gln Ser Tyr Leu Ser Ser<br>        580                        585                       590 | 1776 |
| tct atg cca gct ggt tgt gtt ttg cca gta ggt ggt aat ttt gag atc<br>Ser Met Pro Ala Gly Cys Val Leu Pro Val Gly Gly Asn Phe Glu Ile<br>595                                  600                       605 | 1824 |
| ttg tta cat tac tat ctt ctc aat tat gcc aaa aaa tgc cat caa tca<br>Leu Leu His Tyr Tyr Leu Leu Asn Tyr Ala Lys Lys Cys His Gln Ser<br>610                                  615                       620 | 1872 |
| gaa gaa acc atg gtt agt atg ata ata gct aat gca ctt tta ggc att<br>Glu Glu Thr Met Val Ser Met Ile Ile Ala Asn Ala Leu Leu Gly Ile<br>625                                  630                       635                   640 | 1920 |

-continued

| | |
|---|---|
| ccc aaa gtc ctt tat aaa tct aaa aca gga aag tac agc ttt cca cat<br>Pro Lys Val Leu Tyr Lys Ser Lys Thr Gly Lys Tyr Ser Phe Pro His<br>                                  645                            650                      655 | 1968 |
| aca tat ata aga gct gtc cat gca ctg caa acc aat caa ccc ttg gta<br>Thr Tyr Ile Arg Ala Val His Ala Leu Gln Thr Asn Gln Pro Leu Val<br>                660                            665                            670 | 2016 |
| agc agt cag aca ggt ttg gaa tca gta atg ggt aaa tac cag cta cta<br>Ser Ser Gln Thr Gly Leu Glu Ser Val Met Gly Lys Tyr Gln Leu Leu<br>        675                            680                            685 | 2064 |
| act tca gtt ctt cag tgt ttg aca aaa ata tta acc att gac atg gta<br>Thr Ser Val Leu Gln Cys Leu Thr Lys Ile Leu Thr Ile Asp Met Val<br>690                            695                            700 | 2112 |
| atc act gtt aag aga cac cct cag aaa gtt cac aat caa gat tca gaa<br>Ile Thr Val Lys Arg His Pro Gln Lys Val His Asn Gln Asp Ser Glu<br>705                            710                            715                            720 | 2160 |
| gat gaa cta taa<br>Asp Glu Leu | 2172 |

<210> SEQ ID NO 2
<211> LENGTH: 723
<212> TYPE: PRT
<213> ORGANISM: Homo sapiens

<400> SEQUENCE: 2

Met Leu Ser Ser Met Ala Ala Gly Ser Val Lys Ala Ala Leu Gln
1               5                   10                  15

Val Ala Glu Val Leu Glu Ala Ile Val Ser Cys Cys Val Gly Pro Glu
                20                  25                  30

Gly Arg Gln Val Leu Cys Thr Lys Pro Thr Gly Glu Val Leu Leu Ser
            35                  40                  45

Arg Asn Gly Gly Arg Leu Leu Glu Ala Leu His Leu Glu His Pro Ile
        50                  55                  60

Ala Arg Met Ile Val Asp Cys Val Ser Ser His Leu Lys Lys Thr Gly
65                  70                  75                  80

Asp Gly Ala Lys Thr Phe Ile Ile Phe Leu Cys His Leu Leu Arg Gly
                85                  90                  95

Leu His Ala Ile Thr Asp Arg Glu Lys Asp Pro Leu Met Cys Glu Asn
            100                 105                 110

Ile Gln Thr His Gly Arg His Trp Lys Asn Cys Ser Arg Trp Lys Phe
        115                 120                 125

Ile Ser Gln Ala Leu Leu Thr Phe Gln Thr Gln Ile Leu Asp Gly Ile
    130                 135                 140

Met Asp Gln Tyr Leu Ser Arg His Phe Leu Ser Ile Phe Ser Ser Ala
145                 150                 155                 160

Lys Glu Arg Thr Leu Cys Arg Ser Ser Leu Gly Leu Leu Leu Glu Ala
                165                 170                 175

Tyr Phe Cys Gly Arg Val Gly Arg Asn Asn His Lys Phe Ile Ser Gln
            180                 185                 190

Leu Met Cys Asp Tyr Phe Phe Lys Cys Met Thr Cys Lys Ser Gly Ile
        195                 200                 205

Gly Val Phe Glu Leu Val Asp Asp His Phe Val Glu Leu Asn Val Gly
    210                 215                 220

Val Thr Gly Leu Pro Val Ser Asp Ser Arg Ile Ile Ala Gly Leu Val
225                 230                 235                 240

Leu Gln Lys Asp Phe Ser Val Tyr Arg Pro Ala Asp Gly Asp Met Arg
                245                 250                 255

Met Val Ile Val Thr Glu Thr Ile Gln Pro Leu Phe Ser Thr Ser Gly

```
                    260                 265                 270
Ser Glu Phe Ile Leu Asn Ser Glu Ala Gln Phe Gln Thr Ser Gln Phe
                275                 280                 285

Trp Ile Met Glu Lys Thr Lys Ala Ile Met Lys His Leu His Ser Gln
                290                 295                 300

Asn Val Lys Leu Leu Ile Ser Ser Val Lys Gln Pro Asp Leu Val Ser
305                 310                 315                 320

Tyr Tyr Ala Gly Val Asn Gly Ile Ser Val Val Glu Cys Leu Ser Ser
                325                 330                 335

Glu Glu Val Ser Leu Ile Arg Arg Ile Ile Gly Leu Ser Pro Phe Val
                340                 345                 350

Pro Pro Gln Ala Phe Ser Gln Cys Glu Ile Pro Asn Thr Ala Leu Val
                355                 360                 365

Lys Phe Cys Lys Pro Leu Ile Leu Arg Ser Lys Arg Tyr Val His Leu
                370                 375                 380

Gly Leu Ile Ser Thr Cys Ala Phe Ile Pro His Ser Ile Val Leu Cys
385                 390                 395                 400

Gly Pro Val His Gly Leu Ile Glu Gln His Glu Asp Ala Leu His Gly
                405                 410                 415

Ala Leu Lys Met Leu Arg Gln Leu Phe Lys Asp Leu Asp Leu Asn Tyr
                420                 425                 430

Met Thr Gln Thr Asn Asp Gln Asn Gly Thr Ser Ser Leu Phe Ile Tyr
                435                 440                 445

Lys Asn Ser Gly Glu Ser Tyr Gln Ala Pro Asp Pro Gly Asn Gly Ser
450                 455                 460

Ile Gln Arg Pro Tyr Gln Asp Thr Val Ala Glu Asn Lys Asp Ala Leu
465                 470                 475                 480

Glu Lys Thr Gln Thr Tyr Leu Lys Val His Ser Asn Leu Val Ile Pro
                485                 490                 495

Asp Val Glu Leu Glu Thr Tyr Ile Pro Tyr Ser Thr Pro Thr Leu Thr
                500                 505                 510

Pro Thr Asp Thr Phe Gln Thr Val Glu Thr Leu Thr Cys Leu Ser Leu
                515                 520                 525

Glu Arg Asn Arg Leu Thr Asp Tyr Tyr Glu Pro Leu Leu Lys Asn Asn
                530                 535                 540

Ser Thr Ala Tyr Ser Thr Arg Gly Asn Arg Ile Glu Ile Ser Tyr Glu
545                 550                 555                 560

Asn Leu Gln Val Thr Asn Ile Thr Arg Lys Gly Ser Met Leu Pro Val
                565                 570                 575

Ser Cys Lys Leu Pro Asn Met Gly Thr Ser Gln Ser Tyr Leu Ser Ser
                580                 585                 590

Ser Met Pro Ala Gly Cys Val Leu Pro Val Gly Gly Asn Phe Glu Ile
                595                 600                 605

Leu Leu His Tyr Tyr Leu Leu Asn Tyr Ala Lys Lys Cys His Gln Ser
                610                 615                 620

Glu Glu Thr Met Val Ser Met Ile Ile Ala Asn Ala Leu Leu Gly Ile
625                 630                 635                 640

Pro Lys Val Leu Tyr Lys Ser Lys Thr Gly Lys Tyr Ser Phe Pro His
                645                 650                 655

Thr Tyr Ile Arg Ala Val His Ala Leu Gln Thr Asn Gln Pro Leu Val
                660                 665                 670

Ser Ser Gln Thr Gly Leu Glu Ser Val Met Gly Lys Tyr Gln Leu Leu
                675                 680                 685
```

```
Thr Ser Val Leu Gln Cys Leu Thr Lys Ile Leu Thr Ile Asp Met Val
        690             695                 700

Ile Thr Val Lys Arg His Pro Gln Lys Val His Asn Gln Asp Ser Glu
705                 710                 715                 720

Asp Glu Leu

<210> SEQ ID NO 3
<211> LENGTH: 1974
<212> TYPE: DNA
<213> ORGANISM: Homo sapiens
<220> FEATURE:
<221> NAME/KEY: CDS
<222> LOCATION: (1)..(1971)

<400> SEQUENCE: 3 atg ata gtg gac tgt gtt tcc agt cat ctc aaa aaa aca gga gat ggt      48
Met Ile Val Asp Cys Val Ser Ser His Leu Lys Lys Thr Gly Asp Gly
  1               5                  10                  15 gca aaa aca ttt att atc ttt ctt tgc cat ttg ctt aga gga ctt cat      96
Ala Lys Thr Phe Ile Ile Phe Leu Cys His Leu Leu Arg Gly Leu His
                 20                  25                  30 gca atc aca gac aga gaa aag gat cct ttg atg tgt gaa aac att caa     144
Ala Ile Thr Asp Arg Glu Lys Asp Pro Leu Met Cys Glu Asn Ile Gln
             35                  40                  45 acc cat gga agg cat tgg aaa aat tgt tct cgg tgg aaa ttt att tcc     192
Thr His Gly Arg His Trp Lys Asn Cys Ser Arg Trp Lys Phe Ile Ser
 50                  55                  60 cag gct ctc cta acg ttt cag aca caa ata tta gac ggt att atg gac     240
Gln Ala Leu Leu Thr Phe Gln Thr Gln Ile Leu Asp Gly Ile Met Asp
 65                  70                  75                  80 cag tac cta agt aga cac ttt ttg tct atc ttt tcg tct gct aaa gag     288
Gln Tyr Leu Ser Arg His Phe Leu Ser Ile Phe Ser Ser Ala Lys Glu
                 85                  90                  95 aga aca ttg tgt agg agc tct tta gag ttg ctc tta gaa gca tac ttt     336
Arg Thr Leu Cys Arg Ser Ser Leu Glu Leu Leu Leu Glu Ala Tyr Phe
            100                 105                 110 tgt gga aga gtg gga aga aat aat cat aaa ttt att tca cag ttg atg     384
Cys Gly Arg Val Gly Arg Asn Asn His Lys Phe Ile Ser Gln Leu Met
        115                 120                 125 tgt gac tac ttt ttc aag tgt atg act tgt aaa agt ggg att ggt gta     432
Cys Asp Tyr Phe Phe Lys Cys Met Thr Cys Lys Ser Gly Ile Gly Val
    130                 135                 140 ttt gag tta gtg gat gac cat ttt gta gag ttg aat gtt ggt gtc act     480
Phe Glu Leu Val Asp Asp His Phe Val Glu Leu Asn Val Gly Val Thr
145                 150                 155                 160 ggc ctt cct gtt tca gat tcc agg atc ata gct ggt ctt gtg ctt cag     528
Gly Leu Pro Val Ser Asp Ser Arg Ile Ile Ala Gly Leu Val Leu Gln
                165                 170                 175 aaa gat ttt tct gtg tac cgc cca gca gat ggt gac atg cga atg gtg     576
Lys Asp Phe Ser Val Tyr Arg Pro Ala Asp Gly Asp Met Arg Met Val
            180                 185                 190 ata gta aca gaa acc att cag cct ctt ttt tcc act tct gga tca gag     624
Ile Val Thr Glu Thr Ile Gln Pro Leu Phe Ser Thr Ser Gly Ser Glu
        195                 200                 205 ttt att cta aat tca gaa gca cag ttt cag aca tct caa ttt tgg att     672
Phe Ile Leu Asn Ser Glu Ala Gln Phe Gln Thr Ser Gln Phe Trp Ile
    210                 215                 220 atg gaa aag aca aaa gca ata atg aaa cat cta cat agt cag aat gta     720
Met Glu Lys Thr Lys Ala Ile Met Lys His Leu His Ser Gln Asn Val
225                 230                 235                 240 aaa ttg ctc ata tct agt gtg aaa caa cca gat tta gtt agt tat tat     768
```

-continued

```
                Lys Leu Leu Ile Ser Ser Val Lys Gln Pro Asp Leu Val Ser Tyr Tyr
                                245                 250                 255 gca ggg gtg aat ggc ata tca gtg gtt gag tgt tta tca tca gaa gaa          816
Ala Gly Val Asn Gly Ile Ser Val Val Glu Cys Leu Ser Ser Glu Glu
            260                 265                 270 gtt tct ctt atc cgg agg atc att ggt ctt tct cca ttt gta cca cca          864
Val Ser Leu Ile Arg Arg Ile Ile Gly Leu Ser Pro Phe Val Pro Pro
        275                 280                 285 cag gcc ttt tcg cag tgt gaa ata cct aac act gct ttg gtg aaa ttt          912
Gln Ala Phe Ser Gln Cys Glu Ile Pro Asn Thr Ala Leu Val Lys Phe
    290                 295                 300 tgt aaa cct ctt atc ctt aga tcc aaa aga tat gtt cat cta ggc ttg          960
Cys Lys Pro Leu Ile Leu Arg Ser Lys Arg Tyr Val His Leu Gly Leu
305                 310                 315                 320 ata agc aca tgt gca ttt ata cca cac tct ata gtt ctt tgt gga cca         1008
Ile Ser Thr Cys Ala Phe Ile Pro His Ser Ile Val Leu Cys Gly Pro
                325                 330                 335 gtg cat ggt ctc att gaa caa cat gag gat gct tta cat gga gca ctt         1056
Val His Gly Leu Ile Glu Gln His Glu Asp Ala Leu His Gly Ala Leu
            340                 345                 350 aaa atg ctt cgg caa tta ttt aaa gac ctt gat cta aat tac atg aca         1104
Lys Met Leu Arg Gln Leu Phe Lys Asp Leu Asp Leu Asn Tyr Met Thr
        355                 360                 365 caa acc aat gac caa aat ggc act tca agt ctt ttt att tat aag aac         1152
Gln Thr Asn Asp Gln Asn Gly Thr Ser Ser Leu Phe Ile Tyr Lys Asn
    370                 375                 380 agt gga gaa agt tat caa gca cca gat cct ggt aat ggc tca ata caa         1200
Ser Gly Glu Ser Tyr Gln Ala Pro Asp Pro Gly Asn Gly Ser Ile Gln
385                 390                 395                 400 agg cct tat cag gac aca gtt gca gag aac aaa gat gca ttg gaa aaa         1248
Arg Pro Tyr Gln Asp Thr Val Ala Glu Asn Lys Asp Ala Leu Glu Lys
                405                 410                 415 act caa aca tat tta aaa gta cat tct aat ttg gta att cca gat gta         1296
Thr Gln Thr Tyr Leu Lys Val His Ser Asn Leu Val Ile Pro Asp Val
            420                 425                 430 gaa tta gaa aca tat att ccg tat tca acc ccc aca ctg aca cca aca         1344
Glu Leu Glu Thr Tyr Ile Pro Tyr Ser Thr Pro Thr Leu Thr Pro Thr
        435                 440                 445 gat aca ttc caa aca gtt gaa acg ctg aca tgt ttg tct ttg gaa aga         1392
Asp Thr Phe Gln Thr Val Glu Thr Leu Thr Cys Leu Ser Leu Glu Arg
    450                 455                 460 aac agg cta act gat tat tat gaa cca tta ctc aag aac aat tcc act         1440
Asn Arg Leu Thr Asp Tyr Tyr Glu Pro Leu Leu Lys Asn Asn Ser Thr
465                 470                 475                 480 gct tat tca aca agg gga aat aga ata gaa att tct tac gaa aat tta         1488
Ala Tyr Ser Thr Arg Gly Asn Arg Ile Glu Ile Ser Tyr Glu Asn Leu
                485                 490                 495 cag gtc aca aat att act aga aag gga agc atg tta cca gtg agc tgt         1536
Gln Val Thr Asn Ile Thr Arg Lys Gly Ser Met Leu Pro Val Ser Cys
            500                 505                 510 aag tta ccg aat atg ggt act tcc cag agt tac ctt tcc tca tct atg         1584
Lys Leu Pro Asn Met Gly Thr Ser Gln Ser Tyr Leu Ser Ser Ser Met
        515                 520                 525 cca gct ggt tgt gtt ttg cca gta ggt ggt aat ttt gag atc ttg tta         1632
Pro Ala Gly Cys Val Leu Pro Val Gly Gly Asn Phe Glu Ile Leu Leu
    530                 535                 540 cat tac tat ctt ctc aat tat gcc aaa aaa tgc cat caa tca gaa gaa         1680
His Tyr Tyr Leu Leu Asn Tyr Ala Lys Lys Cys His Gln Ser Glu Glu
545                 550                 555                 560 acc atg gtt agt atg ata ata gct aat gca ctt tta ggc att ccc aaa         1728
```

```
                Thr Met Val Ser Met Ile Ile Ala Asn Ala Leu Leu Gly Ile Pro Lys
                                565                 570                 575 gtc ctt tat aaa tct aaa aca gga aag tac agc ttt cca cat aca tat        1776
Val Leu Tyr Lys Ser Lys Thr Gly Lys Tyr Ser Phe Pro His Thr Tyr
            580                 585                 590 ata aga gct gtc cat gca ctg caa acc aat caa ccc ttg gta agc agt        1824
Ile Arg Ala Val His Ala Leu Gln Thr Asn Gln Pro Leu Val Ser Ser
        595                 600                 605 cag aca ggt ttg gaa tca gta atg ggt aaa tac cag cta cta act tca        1872
Gln Thr Gly Leu Glu Ser Val Met Gly Lys Tyr Gln Leu Leu Thr Ser
    610                 615                 620 gtt ctt cag tgt ttg aca aaa ata tta acc att gac atg gta atc act        1920
Val Leu Gln Cys Leu Thr Lys Ile Leu Thr Ile Asp Met Val Ile Thr
625                 630                 635                 640 gtt aag aga cac cct cag aaa gtt cac aat caa gat tca gaa gat gaa        1968
Val Lys Arg His Pro Gln Lys Val His Asn Gln Asp Ser Glu Asp Glu
                645                 650                 655 cta taa                                                                 1974
Leu <210> SEQ ID NO 4
<211> LENGTH: 657
<212> TYPE: PRT
<213> ORGANISM: Homo sapiens

<400> SEQUENCE: 4

Met Ile Val Asp Cys Val Ser Ser His Leu Lys Lys Thr Gly Asp Gly
  1               5                  10                  15

Ala Lys Thr Phe Ile Ile Phe Leu Cys His Leu Leu Arg Gly Leu His
                 20                  25                  30

Ala Ile Thr Asp Arg Glu Lys Asp Pro Leu Met Cys Glu Asn Ile Gln
             35                  40                  45

Thr His Gly Arg His Trp Lys Asn Cys Ser Arg Trp Lys Phe Ile Ser
         50                  55                  60

Gln Ala Leu Leu Thr Phe Gln Thr Gln Ile Leu Asp Gly Ile Met Asp
 65                  70                  75                  80

Gln Tyr Leu Ser Arg His Phe Leu Ser Ile Phe Ser Ser Ala Lys Glu
                 85                  90                  95

Arg Thr Leu Cys Arg Ser Ser Leu Glu Leu Leu Leu Glu Ala Tyr Phe
            100                 105                 110

Cys Gly Arg Val Gly Arg Asn Asn His Lys Phe Ile Ser Gln Leu Met
        115                 120                 125

Cys Asp Tyr Phe Phe Lys Cys Met Thr Cys Lys Ser Gly Ile Gly Val
    130                 135                 140

Phe Glu Leu Val Asp Asp His Phe Val Glu Leu Asn Val Gly Val Thr
145                 150                 155                 160

Gly Leu Pro Val Ser Asp Ser Arg Ile Ile Ala Gly Leu Val Leu Gln
                165                 170                 175

Lys Asp Phe Ser Val Tyr Arg Pro Ala Asp Gly Asp Met Arg Met Val
            180                 185                 190

Ile Val Thr Glu Thr Ile Gln Pro Leu Phe Ser Thr Ser Gly Ser Glu
        195                 200                 205

Phe Ile Leu Asn Ser Glu Ala Gln Phe Gln Thr Ser Gln Phe Trp Ile
    210                 215                 220

Met Glu Lys Thr Lys Ala Ile Met Lys His Leu His Ser Gln Asn Val
225                 230                 235                 240

Lys Leu Leu Ile Ser Ser Val Lys Gln Pro Asp Leu Val Ser Tyr Tyr
```

-continued

```
                245                 250                 255
Ala Gly Val Asn Gly Ile Ser Val Val Glu Cys Leu Ser Ser Glu Glu
            260                 265                 270

Val Ser Leu Ile Arg Arg Ile Ile Gly Leu Ser Pro Phe Val Pro Pro
            275                 280             285

Gln Ala Phe Ser Gln Cys Glu Ile Pro Asn Thr Ala Leu Val Lys Phe
            290                 295             300

Cys Lys Pro Leu Ile Leu Arg Ser Lys Arg Tyr Val His Leu Gly Leu
305             310                 315                 320

Ile Ser Thr Cys Ala Phe Ile Pro His Ser Ile Val Leu Cys Gly Pro
                325                 330                 335

Val His Gly Leu Ile Glu Gln His Glu Asp Ala Leu His Gly Ala Leu
            340                 345                 350

Lys Met Leu Arg Gln Leu Phe Lys Asp Leu Asp Leu Asn Tyr Met Thr
            355                 360                 365

Gln Thr Asn Asp Gln Asn Gly Thr Ser Ser Leu Phe Ile Tyr Lys Asn
            370                 375             380

Ser Gly Glu Ser Tyr Gln Ala Pro Asp Pro Gly Asn Gly Ser Ile Gln
385             390                 395                 400

Arg Pro Tyr Gln Asp Thr Val Ala Glu Asn Lys Asp Ala Leu Glu Lys
                405                 410                 415

Thr Gln Thr Tyr Leu Lys Val His Ser Asn Leu Val Ile Pro Asp Val
            420                 425                 430

Glu Leu Glu Thr Tyr Ile Pro Tyr Ser Thr Pro Thr Leu Thr Pro Thr
            435                 440                 445

Asp Thr Phe Gln Thr Val Glu Thr Leu Thr Cys Leu Ser Leu Glu Arg
            450                 455                 460

Asn Arg Leu Thr Asp Tyr Tyr Glu Pro Leu Leu Lys Asn Asn Ser Thr
465             470                 475                 480

Ala Tyr Ser Thr Arg Gly Asn Arg Ile Glu Ile Ser Tyr Glu Asn Leu
                485                 490                 495

Gln Val Thr Asn Ile Thr Arg Lys Gly Ser Met Leu Pro Val Ser Cys
            500                 505                 510

Lys Leu Pro Asn Met Gly Thr Ser Gln Ser Tyr Leu Ser Ser Ser Met
            515                 520                 525

Pro Ala Gly Cys Val Leu Pro Val Gly Gly Asn Phe Glu Ile Leu Leu
            530                 535             540

His Tyr Tyr Leu Leu Asn Tyr Ala Lys Lys Cys His Gln Ser Glu Glu
545             550                 555                 560

Thr Met Val Ser Met Ile Ile Ala Asn Ala Leu Leu Gly Ile Pro Lys
                565                 570                 575

Val Leu Tyr Lys Ser Lys Thr Gly Lys Tyr Ser Phe Pro His Thr Tyr
            580                 585                 590

Ile Arg Ala Val His Ala Leu Gln Thr Asn Pro Leu Val Ser Ser
            595                 600                 605

Gln Thr Gly Leu Glu Ser Val Met Gly Lys Tyr Gln Leu Leu Thr Ser
            610                 615                 620

Val Leu Gln Cys Leu Thr Lys Ile Leu Thr Ile Asp Met Val Ile Thr
625             630                 635                 640

Val Lys Arg His Pro Gln Lys Val His Asn Gln Asp Ser Glu Asp Glu
                645                 650                 655

Leu
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
gaagccgtgc taccccggct    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
cgcatcgcct caggatggga    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
gatgtgggaa gccagccttc    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
ggccagtgac accaacattc    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
cacagttgat gtgtgactac    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
ttcaccaaag cagtgttagg    20

<210> SEQ ID NO 11
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tccggaggat cattggtctt                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
catgtcagcg tttcaactgt                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caggacacag ttgcagagaa                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcagtgcatg gacagctctt                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cctcatctat gccagctggt                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
accagtggtc acatgactgc                                               20

<210> SEQ ID NO 17
<211> LENGTH: 37
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 17
tgtaaaacga cggccagtgg ttttctcccc gcctatt                              37

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caggaaacag ctatgacctc acccgaggtc agtctttc                             38

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgtaaaacga cggccagtga tgtatccaag gaacaatatt ctca                      44

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
caggaaacag ctatgacctt tcttcccact cttccacaa                            39

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgtaaaacga cggccagtga cggtattatg gaccagtacc                           40

<210> SEQ ID NO 22
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caggaaacag ctatgacctg agcaatttta cattctgact atg                       43

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic
```

```
                      primer

<400> SEQUENCE: 23
tgtaaaacga cggccagtca gaaaccattc agcctctttt                              40

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caggaaacag ctatgaccgg tctttaaata attgccgaag c                           41

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgtaaaacga cggccagttc caaaagatat gttcatctag gc                          42

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
caggaaacag ctatgaccaa gcagtggaat tgttcttgag                              40

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgtaaaacga cggccagtcc aaacagttga aacgctga                               38

<210> SEQ ID NO 28
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
caggaaacag ctatgaccat tggtttgcag tgcatgg                                37

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 29
tgtaaaacga cggccagttt taggcattcc caaagtcc                              38

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
caggaaacag ctatgaccgg tctggtgacc ttagtgtgc                             39

<210> SEQ ID NO 31
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cagtcatctc a                                                          11

<210> SEQ ID NO 32
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcagagaaca aag                                                        13

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Thr or Ser

<400> SEQUENCE: 33

Gly Asp Gly Thr Thr Xaa
  1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ala, Val, Ser or Thr
<220> FEATURE:
<221> NAME/KEY: MOD_RES
<222> LOCATION: (6)..(6)
<223> OTHER INFORMATION: Thr or Ser
```

```
<400> SEQUENCE: 34

Gly Asp Gly Xaa Lys Xaa
 1               5
```

US 8,163,482 B2

BBS10 RELATED DIAGNOSTIC METHODS FOR BARDET-BIEDL SYNDROME

The present application claims priority to U.S. Provisional Patent Application Ser. No. 60/776,188 filed on Feb. 23, 2006, the entire content of which is specifically incorporated herein by reference.

BACKGROUND OF THE INVENTION

Bardet-Biedl Syndrome (BBS; OMIM 209900) is a rare, autosomal recessive disorder characterized by a multitude of signs, most prominently a progressive retinal dystrophy, postnatal obesity, polydactyly (one or more extra digits), cognitive impairment, and renal dysplasia.

The incidence of BBS varies between populations. A relatively high incidence of BBS is found in the mixed Arab populations of Kuwait and the Bedouin tribes throughout the Middle East, most likely due to the high rate of consanguinity in these populations. A relatively high frequency of BBS has also been reported in New Foundland.

BBS has been shown to display a remarkable degree of non-allelic genetic heterogeneity. The disorder was first shown to be genetically heterogenous based on mapping studies performed in large inbred Bedouin kindreds from Israel. The large number of traditional consanguineous marriages within these groups make it possible to identify inbred kindreds with multiple affected individuals that are large enough for independent linkage analysis.

The first BBS locus (now referred to as BBS2) was mapped to chromosome 16 using a large inbred Bedouin kindred. Genetic heterogeneity was demonstrated when a second Bedouin BBS kindred did not map to the chromosome 16 locus. Subsequent studies in the second Bedouin kindred revealed linkage to chromosome 3 (BBS3). A third Bedouin kindred showed linkage to chromosome 15 (BBS4).

To date, studies have demonstrated the existence of nine BBS loci (BBS1-9). A locus on chromosome 11 was assigned the designation BBS1 based on the fact that it appears to be the most common known cause of BBS in some populations, mutated in ~24% of Caucasians but infrequently in other populations. Each of the other eight genes accounts for <5% of the total mutational load. These nine BBS genes explain only 40-50% of the total mutational load. In about half of BBS families, no mutations have been identified, indicating the presence of other, yet unidentified, BBS genes.

Thus there exists a need for identifying new BBS genes and compositions and assays that are useful in the diagnosis and treatment of BBS. The identification of new BBS genes may further provide important insight into biochemical and developmental pathways involved in common complex disorders including obesity and diabetes mellitus.

SUMMARY OF THE INVENTION

Provided herein are isolated nucleic acids comprising a nucleotide sequence that is at least about 90%, 95%, 98%, or 99% identical to SEQ ID NO: 1 or 3 or to an allele thereof that comprises one or more nucleotide changes set forth in FIG. 1, 5, 6 or 9. Other nucleic acids comprise a nucleotide sequence encoding a polypeptide that is at least about 90%, 95%, 98%, or 99% identical to SEQ ID NO: 2 or 4 or to a variant thereof that comprises one or more amino acid changes set forth in FIG. 1, 5, 6 or 9. Also provided are nucleic acids that hybridize under stringent conditions to a nucleic acid consisting of a nucleotide sequence set forth in SEQ ID NO: 1 or 3 or to an allele thereof that comprises one or more nucleotide changes set forth in FIG. 1, 5, 6 or 9. Other nucleic acids include those that hybridize under stringent conditions to a nucleic acid encoding a polypeptide comprising SEQ ID NO: 2 or 4 or a variant thereof that comprises one or more amino acid changes set forth in FIG. 1, 5, 6 or 9.

Further provided are isolated nucleic acids comprising a nucleotide sequence of SEQ ID NO: 1 or 3 or an allele thereof that comprises one or more nucleotide changes set forth in FIG. 1, 5, 6 or 9, wherein the nucleic acid encompasses one or more nucleotides set forth in FIG. 1, 5, 6 or 9. The one or more nucleotides may be those that are present in the wild-type gene, e.g., SEQ ID NO: 1 or 3, or those that are present in the disease associated allele of the gene. Nucleic acid acids or sequences thereof may consist of about 10-50, 10-100, 10-200, 10-300, 10-400 or more nucleotides. Also provided are isolated nucleic acids consisting of about 10 to 50 nucleotides, which nucleic acids hybridize under stringent conditions to the isolated nucleic acid of claim 5. Stringent hybridization or washing conditions may include, e.g., 2×SSC and a temperature of 50, 60 or 65° C. Other nucleic acids provided herein are those that consist essentially of a nucleotide sequence of about 10 to 50 consecutive nucleotides of SEQ ID NO: 1 or 3, wherein the nucleotide sequence is located adjacent to a nucleotide change set forth in FIG. 1, 5, 6 or 9, or the complement thereof. For example, a nucleotide sequence may be located within about 10 to 50 nucleotides from the nucleotide change. The nucleic acids may be used as probes or primers in diagnostic or prognostic methods. The complements of any of these nucleic acids are also encompassed herein. The nucleic acids may also be part of a composition, e.g., a composition comprising two isolated nucleic acids. A nucleic acid may also be linked to a non-nucleic acid moiety, e.g., a label, such as biotin, or it may be linked to a heterologous nucleic acid. Some nucleic acids do not encompass the full length nucleotide sequence set forth in SEQ ID NO: 1 or 3.

Also described herein are polypeptides, e.g., those that are encoded by a nucleic acid described herein and/or which comprise one or more amino acid changes set forth in FIG. 1, 5, 6 or 9. Furthermore, antibodies that binds specifically to a polypeptide described herein are provided. An antibody may bind to an epitope of a polypeptide comprising an amino acid sequence set forth in FIG. 1, 5, 6 or 9. The amino acid may be an amino acid of a disease associated variant or that of a wild-type protein, e.g., consisting of SEQ ID NO: 2 or 4. An antibody may be linked to a moiety, e.g., a label, such as when an antibody is used in diagnostic or prognostic methods.

Kits are also encompassed. Exemplary kits comprise one or more nucleic acids, polypeptides or antibodies described herein. A kit may further comprise one or more other nucleic acids, polypeptides or antibodies described herein and/or one or more reagents for use in a diagnostic assay.

Encompassed herein are methods for determining the presence of a mutated BBS10 and optionally for detecting mutations in other BBS proteins in DNA or proteins, a cell a cell extract or a portion thereof.

Disclosed herein are diagnostic and prognostic methods, e.g., for determining whether a subject has or is likely to develop a disease associated with a mutation in BBS10, such as BBS, obesity, diabetes mellitus, retinopathy, renal malformation, renal dysfunctions, hypogonadism, mental retardation, or polydactyly. A method may comprise providing a sample of a subject comprising a BBS10 nucleic acid or a portion thereof and determining whether the BBS10 nucleic acid or portion thereof comprises a nucleotide sequence that differs from SEQ ID NO: 1 or 3, wherein the presence of a nucleotide sequence that differs from SEQ ID NO: 1 or 3 and is not a polymorphic variation indicates that the subject has or is likely to develop a disease associated with a mutation in BBS10. The nucleotide sequence of the BBS10 nucleic acid or portion thereof may differ from SEQ ID NO: 1 or 3 in one or more nucleotides set forth in FIG. 1, 5, 6 or 9. The method may comprise determining whether the BBS10 nucleic acid or portion thereof comprises one or more nucleotides set forth in FIG. 1, 5, 6 or 9 that are associated with a disease. A method may comprise determining whether the BBS10 nucleic acid or portion thereof comprises two mutations set forth in FIG. 1, 5, 6 or 9. A method may comprise determining whether the subject is homozygous for a mutation set forth in FIG. 1, 5, 6 or 9. A method may comprise determining whether the subject has a genetic profile set forth in FIG. 5. A method may comprise determining whether the BBS10 nucleic acid or portion thereof comprises one mutation set forth in FIG. 1, 5, 6 or 9 and a second mutation in another BBS nucleic acid.

Other methods for determining whether a subject has or is likely to develop a disease associated with a mutation in BBS10 may comprise providing a sample of a subject comprising a BBS10 polypeptide or a portion thereof and determining whether the BBS10 polypeptide or portion thereof comprises an amino acid sequence that differs from SEQ ID NO: 2 or 4, wherein the presence of an amino acid sequence that differs from SEQ ID NO: 2 or 4 indicates that the subject has or is likely to develop a disease associated with a mutation in BBS10. The amino acid sequence of the BBS10 polypeptide or portion thereof may differ from SEQ ID NO: 2 or 4 in one or more amino acids set forth in FIG. 1, 5, 6 or 9. A method may comprise determining whether the BBS10 polypeptide or portion thereof comprises one or more amino acids set forth in FIG. 1, 5 or 6 that are associated with a disease. A method may comprise determining whether the BBS10 polypeptide or portion thereof comprises two mutations set forth in FIG. 1, 5, 6 or 9. A method may comprise determining whether the subject is homozygous for a mutation set forth in FIG. 1, 5, 6 or 9. A method may comprise determining whether the subject has a genetic profile set forth in FIG. 5. A method may comprise determining whether the BBS10 polypeptide or portion thereof comprises one mutation set forth in FIG. 1, 5, 6 or 9 and a second mutation in another BBS polypeptide. When detecting a mutation in BBS10 and another BBS nucleic acid or polypeptide, the other BBS nucleic acid or polypeptide is BBS 1, 6 or 10.

Also encompassed herein are methods for treating a subject having a disease associated with a mutation in BBS10. A method may comprise administering to a subject in need thereof a therapeutically effective amount of an agent that compensates for the lack of sufficient biologically active BBS10 protein. An agent may be a protein comprising an amino acid sequence that is at least about 90%, 95%, 98% or 99% identical to SEQ ID NO: 2 or 4 or a portion thereof and has a biologic activity that is essentially identical to that of a wild-type BBS10 protein, or a nucleic acid encoding the protein. The agent may also be a nucleic acid comprising a nucleotide sequence that is at least about 90%, 95%, 98% or 99% identical to SEQ ID NO: 1 or 3 or a portion thereof.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2 shows modeling BBS10 loss of function in zebrafish. (a) Live side (upper row) and dorsal (lower row) images of mid-somitic (8-10 somites) embryos. Compared to control embryos of the same somitic age (extreme left), bbs10 morphants ($2^{nd}$, $3^{rd}$ and $4^{th}$ embryos) exhibit a range of developmental defects. Note the shortening of the body axis (all morphants), dorsal thinning ($4^{th}$ embryo), increased somitic length ($3^{rd}$ and $4^{th}$ embryos), poor somitic definition (all embryos) and various defects of the notochord (all embryos). (b) bbs10 interacts genetically with each of bbs1, bbs4 and bbs6. When compared to the range and penetrance of the phenotype of single bbs1, bbs4 and bbs6 morphants, addition of a subeffective dose of bbs10 morpholino exacerbates the bbs-established phenotypes.

FIG. 3 shows the nucleotide and amino acid sequences of the long form of BBS10 (SEQ ID NOs: 1 and 2, respectively).

FIG. 4 shows the nucleotide and amino acid sequences of the short form of BBS10 (SEQ ID NOs: 3 and 4, respectively).

FIG. 5 shows the mutations detected in BBS1O. Amino acid positions are those in the long form of BBS10, SEQ ID NO: 2. "fs" refers to "frameshift" and "X" indicates the amino acid residue that has been changed into a stop codon. Although the missense mutations have not been found in 192 control chromosomes, and represent in almost all cases non conservative chemical changes, we cannot exclude that a few of the missense mutations are not fully pathogenic or may represent normal rare variants (especially Y613H found only once in the heterozygous state). *AR, KK, KF families denote the US cohort, families beginning with roman numerals denote the French cohort, and families beginning with PB denote the UK cohort.  1.5; 11.6; III. 11; V.23; VII.1; VII. 12; AR83-03; AR257-03; AR349-04; AR707-04; AR201-05; AR323-03; AR332-04; AR711-03; PB15.1; PB72.1; PB159.1; PB233.1* V.14; AR736-03; AR234-02; AR371-03; KF02-01. #: segregation data suggest that these variants are not fully pathogenic. In the double mutant L308F/K579R, the latter change is less likely to be pathogenic. Light grey shading indicates homozygote families, dark grey shading indicates the common C91 fsX95 mutation.

FIG. 6 shows likely polymorphisms detected in BBS10. Nucleotide and amino acid positions are those in the long form of BBS10, SEQ ID NOs: 1 and 2, respectively. "1-52" refers to nucleotide 52 upstream of the ATG start codon.

FIG. 8 shows comparative sequence identities and similarities of known BBS genes.

FIG. 9 shows the amino acid and nucleotide changes in BBS patients.

FIG. 10 shows the nucleotide and amino acid changes found in BBS 1, 4, 6 and 7.

DESCRIPTION OF ILLUSTRATIVE EMBODIMENTS

Figure 1A:
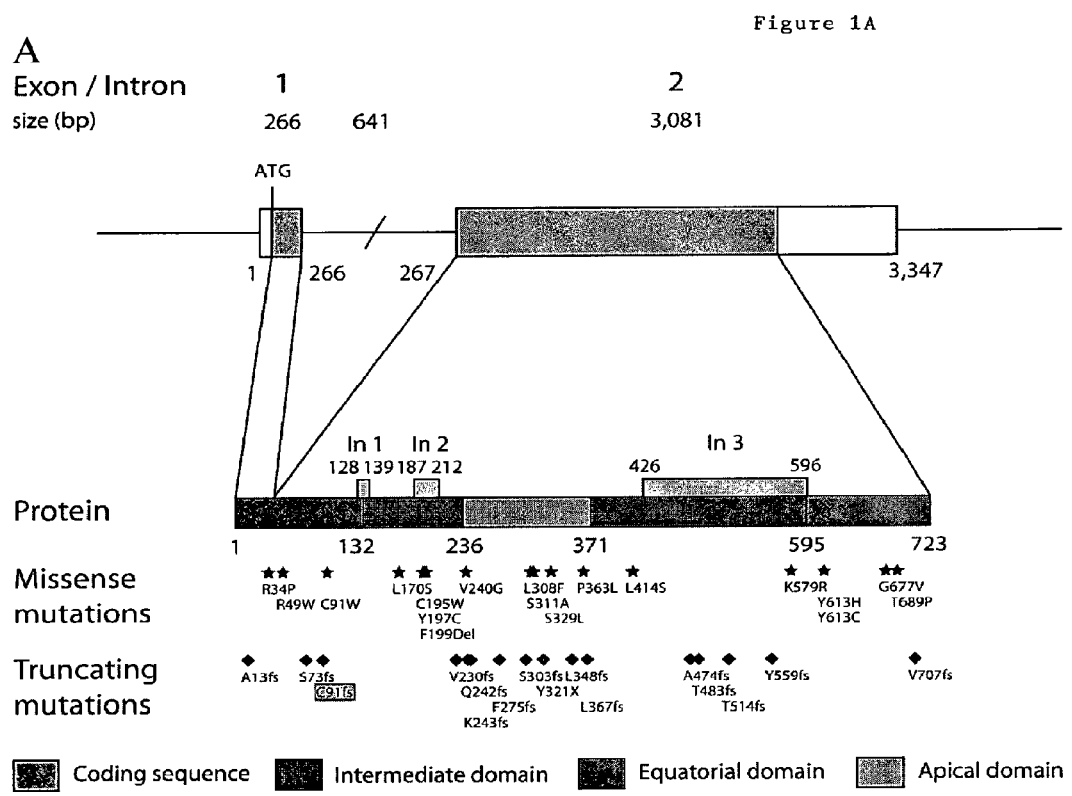
FIG. 1 depicts a schematic of the BBS10 locus and the position/nature of mutations. (a) Shown on top is the BBS10 genomic locus corresponding to the FLJ23560 transcript (RefSeq NM_024685). While FLJ23560 was annotated as a protein of 657 aa (Uniprot Q8TAM1_HUMAN) encoded solely by exon 2, an upstream initiation site in FLJ23560 mRNA is encoded by exon 1. This is supported by multiple sequence alignment with other members of the family (e.g. Q5R8P3_PONPY from *P. pygmaeus*). The size of FLJ23560 is thus 723 aa. The bottom section shows a schematic of the protein with the recognized domains encoded in different colors (see key). The insertions in the intermediate domain are shown as yellow boxes above the protein. All reported mutant alleles are shown underneath the protein; the common frameshift C91fsX95 is highlighted. (b) Ribbon drawing of group II chaperonin alpha subunit (PDB 1q2v). Domains are colored according to FIG. 1a. BBS10 insertions (In1-3) relative to all group II chaperonin sequences are represented as yellow dashed rectangles. (c) Phylogenetic tree of BBS10 family. The tree contains BBS10 sequences, representative sequences from all group II chaperonins and from BBS6. The BBS10 genes are highlighted with organism's names and predicted sequences are marked with a black star. Organisms abbreviations: (PP) *Ponpy pigmaelus*, (HS) *Homo sapiens*, (CF) *Canis familiaris*, (BT) *Bos taurus*, (MM) *Mus musculus*, (RN) *Rattus norvegicus*, (XL) *Xenopus laevis*, (GG) *Gallus gallus*, (TN) *Tetraodon nigroviridis*, (DR) *Danio rerio*, (TR) *Takifugu rubripes*. Bootstrap values are provided for significant nodes when they are >50%.

Compositions and methods for expressing and using BBS10 nucleotides, proteins and polypeptides are provided. The compositions and methods find use in the diagnosis and treatment of BBS and BBS-related conditions including obesity, retinal degeneration, mental retardation, central nervous system disorders, heart and kidney abnormalities, and the like.

More particularly, BBS10 nucleic acids and polypeptides encoded by BBS10 have been identified that are useful in the diagnosis and treatment of these and a variety of other conditions. The most common wild-type human BBS10 polypeptides and cDNAs are provided as SEQ ID NOs:1-4. Polymorphic variants that do not appear to be linked to BBS or related disorders have been identified.

The compositions and methods of the invention can be used for the diagnosis and treatment of BBS, a disorder having a clinical manifestation of BBS, or any disorder that shares a clinical manifestation of BBS, so long such disorders can be diagnosed and/or treated by the methods and compositions of the invention, in a clinically or experimentally determinable manner.

The identification of BBS10 has immediate implications for the populations that were used in the initial mapping and communities that have a high incidence of the disease. Population-wide carrier testing could now be efficiently performed to accurately identify disease gene carriers. Such a program would have the potential of decreasing the burden of this disorder within communities with a high incidence of BBS. In addition, the present invention also provides the opportunity for drug screening to identify therapeutic agents. These and other embodiments are described in greater detail below.

1. BBS10 Nucleic Acids

Provided herein are wild-type and mutated BBS10 nucleic acids. Wild-type BBS10 nucleic acids include those comprising the nucleotide sequence SEQ ID NO: 1, encoding the long form of human BBS10, and SEQ ID NO: 3, encoding the short form of human BBS10. Mutated BBS10 nucleic acids include those having a nucleotide change set forth in FIG. 1, 5 or 6. Other nucleic acids are those that differ from these in one or more nucleotides, such as nucleic acids that are at least about 90%, 95%, 98%, or 99% identical to these nucleic acids. These and other nucleic acids are further described below.

The present invention concerns DNA segments, isolatable from mammalian cells, such as mouse, rat or human cells, that are free from total genomic DNA and that are capable of expressing a protein, polypeptide or peptide. As used herein, the term "DNA segment" refers to a DNA molecule that has been isolated free of total genomic DNA of a particular species. Therefore, a DNA segment encoding FLJ23560 refers to a DNA segment that contains wild-type, polymorphic or mutant FLJ23560 coding sequences yet is isolated away from, or purified free from, total mammalian genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified BBS10 gene refers to a DNA segment encoding FLJ23560 protein, polypeptide or peptide coding sequences and, in certain aspects, regulatory sequences, isolated substantially away from other naturally-occurring genes or protein encoding sequences. "DNA" includes both genomic sequences, cDNA sequences and engineered segments that express, or may be adapted to express, proteins, polypeptides, domains, peptides, fusion proteins and mutants of FLJ23560 encoded sequences.

"Isolated substantially away from other coding sequences" means that the gene of interest, in this case the BBS10 gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

Fragments of BBS10 nucleic acids are also provided, and are further described herein. Exemplary fragments are about 5-10 nucleotides, about 10-15, 15-20, 20-25, 25-30, 30-50, 5-50, 5-100, 10-50 or 10-100 nucleotides long. Fragments can be used as primers or probes and can be single stranded or double-stranded, and from SEQ ID NO: 1, 3 or the complement thereof.

Nucleic acids can overlap one or more nucleotides that differ in wild-type BBS10 relative to disease associated alleles of the gene ("variable nucleotides"). For example, a nucleic acid maybe about 10-100 nucleotides long with the variable nucleotide located approximately in the middle of the nucleic acid. The variable nucleotide may also be located at the 5' or 3' end of the nucleic acid or anywhere else in the nucleic acid. The sequence of a nucleic acid overlapping one or more variable nucleotides may be that of the wild-type (such as for use as a control) or that of a disease associated allele.

Nucleic acids can also be located adjacent to one or more variable nucleotides, such as for use as primers in amplification procedures. Adjacent can be about 1-5, 5-10, 10-15, 15-20, 20-25, 25-30, 30-50, 5-50, 5-100, 10-50 or 10-100 nucleotides 5' or 3' from a variable nucleotide. Pairs of nucleic acids that are adjacent to one or more variable nucleotides, such as a pair of primers for amplifying a region comprising the one or more variable nucleotides, may be located about 10-25, 10-50, 10-100, 10-200, 10-300, 10-400, 10-500, 10-600, 10-700, 10-800, 10-900, or 10-1000 nucleotides or more way from each other, e.g., the 3' end of the first primer is located about this many nucleotides away from the 5' end of the second primer. Exemplary primers, which have been used for detecting mutations described herein are set forth in the Examples.

GenBank Accession numbers of other human BBS genes are as follows:
BBS1: NM_024649.4→NP_078925.3 (Dec. 10, 2006)
BBS2: NM_031885.2→NP_114091.2 (Nov. 17, 2006)
BBS3: NM_001661; NM_032146; NM_177976
BBS4: NM_033028;
BBS5: NM_152384;
BBS6: NM_018848.2→NP_061336.1 (Nov. 17, 2006) and NM_170784.1→NP_740754.1 (Nov. 17, 2006)
BBS7: NM_176824; NM_018190
BBS8: AY373972
BBS9: NM 014451; NM 198428; NM 001033604; NM 001033605
BBS12: NM_152618.2→NP_689831.2 (Feb. 18, 2007)

A. Variants

In particular embodiments, the invention concerns isolated DNA segments and recombinant vectors incorporating DNA sequences that encode a FLJ23560 protein, polypeptide or peptide that includes within its amino acid sequence a contiguous amino acid sequence in accordance with, or essentially as set forth in, SEQ ID NOs:2 or 4, corresponding to the FLJ23560 designated "human FLJ23560."

The term "a sequence essentially as set forth in SEQ ID NO:2 or 4" means that the sequence substantially corresponds to a portion of SEQ ID NO:2 or 4 and has relatively few amino acids that are not identical to, or a biologically functional equivalent of, the amino acids of SEQ ID NO:2 or 4.

The term "biologically functional equivalent" is well understood in the art and is further defined in detail herein. Accordingly, sequences that have at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferrably about 81% and about 90%; or even more preferably, between about 91% and about 99%; of amino acids that are identical or functionally equivalent to the amino acids of SEQ ID NO:2 or 4 will be sequences that are "essentially as set forth in SEQ ID NO:2 or 4," provided the biological activity of the protein is maintained.

In certain other embodiments, the invention concerns isolated DNA segments and recombinant vectors that include within their sequence a nucleic acid sequence essentially as set forth in SEQ ID NOs:1 or 3. The term "essentially as set forth in SEQ ID NOs:1 or 3" is used in the same sense as described above and means that the nucleic acid sequence substantially corresponds to a portion of SEQ ID NOs:1 or 3 and has relatively few codons that are not identical, or functionally equivalent, to the codons of SEQ ID NOs:1 or 3.

The term "functionally equivalent codon" is used herein to refer to codons that encode the same amino acid, such as the six codons for arginine and serine, and also refers to codons that encode biologically equivalent amino acids. Codon usage for various organisms and organelles as is known in the art, allowing one of skill in the art to optimize codon usage for expression in various organisms using the disclosures herein. Thus, it is contemplated that codon usage may be optimized for other animals, as well as other organisms such as a prokaryote (e.g., an eubacteria, an archaea), an eukaryote (e.g., a protist, a plant, a fungi, an animal), a virus and the like, as well as organelles that contain nucleic acids, such as mitochondria or chloroplasts, based on the preferred codon usage as would be known to those of ordinary skill in the art.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein, polypeptide or peptide activity where an amino acid sequence expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferrably about 81% and about 90%; or even more preferably, between about 91% and about 99%; of nucleotides that are identical to the nucleotides of SEQ ID NO:1 or NO:3 will be sequences that are "essentially as set forth in SEQ ID NO:1 or NO:3."

Also provided herein are polymorphic alleles (alleles with one or more polymorphic variations or nucleotides). Exemplary polymorphisms are set forth in FIG. 6. These do not appear to be pathogenic, i.e., their presence alone may not be indicative of a likelihood to develop BBS. Variations that are pathogenic may be to be those affecting the activity of the BBS10 protein, e.g., its enzymatic activity. Exemplary mutations are set forth in FIGS. 1, 5 and 9.

B. Nucleic Acid Hybidization

The nucleic acid sequences disclosed herein also have a variety of uses, such as for example, utility as probes or primers in nucleic acid hybridization embodiments. Thus, DNA segments that are complementary, or essentially complementary, to the sequence set forth in SEQ ID NO:1 and NO:3 are also provided. Isolated nucleic acids that are complementary to genetic variants of SEQ ID NO: 1 are also provided, which include sequences that are complementary to one or more of the sequences with changes selected from the group consisting of those set forth in FIG. 1, 5 or 6. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of, for example, SEQ ID NO:1 or NO:3 under stringent conditions such as those described herein.

As used herein, "hybridization", "hybridizes" or "capable of hybridizing" is understood to mean the forming of a double or triple stranded molecule or a molecule with partial double or triple stranded nature. The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. For example, a medium stringency condition could be provided by about 0.1 to 0.25 M NaCl at temperatures of about 37° C. to about 55° C. Under these conditions, hybridization may occur even though the sequences of probe and target strand are not perfectly complementary, but are mismatched at one or more positions. In another example, a low stringency condition could be provided by about 0.15 M to about 0.9 M salt, at temperatures ranging from about 20° C. to about 55° C. Of course, it is within the skill of one in the art to further modify the low or high stringency conditions to suite a particular application. For example, in other embodiments, hybridization may be achieved under conditions of, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

Accordingly, the nucleotide sequences of the disclosure may be used for their ability to selectively form duplex molecules with complementary stretches of genes or RNAs or to provide primers for amplification of DNA or RNA from tissues. Depending on the application envisioned, it is preferred to employ varying conditions of hybridization to achieve varying degrees of selectivity of probe towards target sequence.

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

For example, nucleic acid fragments may be prepared that include a contiguous stretch of nucleotides identical to or complementary to SEQ ID NO:1 or NO:3, such as, for example, about 8, about 10 to about 14, or about 15 to about 20 nucleotides, and that are chromosome sized pieces, up to about 1,000,000, about 750,000, about 500,000, about 250, 000, about 100,000, about 50,000, about 20,000, or about 10,000, or about 5,000 base pairs in length, with segments of about 3,000 being preferred in certain cases, as well as DNA segments with total lengths of about 1,000, about 500, about 200, about 100 and about 50 base pairs in length (including all intermediate lengths of these lengths listed above, i.e., any range derivable therein and any integer derivable therein such a range) are also contemplated to be useful.

In another embodiment, there is provided an oligonucleotide of about 10 to about 50 bases comprising at least 10 consecutive bases of SEQ ID NOs:1 or 3, or of a nucleic acid spanning a mutation selected from the group consisting of a mutation listed in FIG. 1, 5 or 6, or the complement thereof. The oligonucleotide may be 10, 15, 20, 25, 30, 35, 40, 45 or 50 bases in length, and may have 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 consecutive bases of SEQ ID NO:1 or NO:3.

For example, it will be readily understood that "intermediate lengths", in these contexts, means any length between the quoted ranges, such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 130, 140, 150, 160, 170, 180, 190, including all integers through the 200-500; 500-1,000; 1,000-2,000; 2,000-3,000; 3,000-5,000; 5,000-10,000 ranges, up to and including sequences of about 12,001, 12,002, 13,001, 13,002, 15,000, 20,000 and the like.

Various nucleic acid segments may be designed based on a particular nucleic acid sequence, and may be of any length. A nucleic acid sequence used as a primer or probe in a diagnostic assay is to include the region of the identified sequence variation as shown in FIG. 1, 5 or 6, or which corresponds to a nucleic acid encoding a mutation as identified in FIG. 1. Depending on the location of the mutation, numeric values may be assigned to a sequence surrounding the mutation. For example, a first selected residue is assigned a numerical value of 1, the second residue is 2, etc., and an algorithm defining all nucleic acid segments can be created: n to n+y where n is an integer from 1 to the last number of the sequence and y is the length of the nucleic acid or region containing the mutation (e.g., including but not limited to SEQ ID NO:1 or NO:3) segment minus one, where n+y does not exceed the last number of the sequence. Thus, for a 10-mer, the nucleic acid segments correspond to bases 1 to 10, 2 to 11, 3 to 12 . . . and/or so on. For a 15-mer, the nucleic acid segments correspond to bases 1 to 15, 2 to 16, 3 to 17 . . . and/or so on. For a 20-mer, the nucleic segments correspond to bases 1 to 20, 2 to 21, 3 to 22 . . . and/or so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

The use of a hybridization probe of between 17 and 100 nucleotides in length, or in some aspect of the invention even up to 1-2 kb or more in length, allows the formation of a duplex molecule that is both stable and selective. Molecules having complementary sequences over stretches greater than 20 bases in length may be used, in order to increase stability and selectivity of the hybrid, and thereby improve the quality and degree of particular hybrid molecules obtained. One may design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

In general, it is envisioned that the hybridization probes described herein will be useful both as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the "G+C" content, type of target nucleic acid, source of nucleic acid, size of hybridization probe, etc.). Following washing of the hybridized surface to remove non-specifically bound probe molecules, hybridization is detected, or even quantified, by means of the label.

Certain nucleic acids may hybridize essentially only to the wild-type BBS10 gene, e.g., comprising SEQ ID NO: 1 or 3 or a genomic fragment comprising such, or to the disease associated allele. Other nucleic acids will hybridize two the wild-type allele and a mutated allele. This may depend upon the hybridization conditions and the length of a nucleic acid. Conditions for achieving allele specific hybridizations are known in the art.

C. Nucleic Acid Amplification

Nucleic acid used as a template for amplification is isolated from cells contained in the biological sample, according to standard methodologies (Sambrook et al., 1989, the contents of which are incorporated herein by reference). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to BBS10 genes are contacted with the isolated nucleic acid under conditions that permit selective hybridization. The term "primer," as defined herein, is meant to encompass any nucleic acid that is capable of priming the synthesis of a nascent nucleic acid in a template-dependent process. Typically, primers are oligonucleotides from ten to twenty or thirty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced. Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, each incorporated herein by reference in entirety.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Gingeras et al., PCT Application WO 88/10315, incorporated herein by reference). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Still other nucleic acid amplification processes may be used in conjunction with the nucleic acid probes provided herein.

D. Nucleic Acid Detection

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

In embodiments wherein nucleic acids are amplified, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., 1989). Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols (See Sambrook et al., 1989). Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods for genetic screening to accurately detect additional mutations in genomic DNA, cDNA or RNA samples may be employed. Historically, a number of different methods have been used to detect point mutations, including denaturing gradient gel electrophoresis ("DGGE"), restriction enzyme polymorphism analysis, chemical and enzymatic cleavage methods, and others. The more common procedures currently in use include direct sequencing of target regions amplified by PCR. (see above) and single-strand conformation polymorphism analysis ("SSCP").

A method of screening for additional point mutations in BBS10 may be based on RNase cleavage of base pair mismatches in RNA/DNA and RNA/RNA heteroduplexes, or other methods known in the art. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. After the RNase cleavage reaction, the RNase is inactivated by proteolytic digestion and organic extraction, and the cleavage products are denatured by heating and analyzed by electrophoresis on denaturing polyacrylamide gels. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

2. FLJ23560 Polypeptides

The polypeptide sequences encoded by the BBS10 gene are provided in SEQ ID NOs:2 and 4. SEQ ID NO: 2 represents the long form of the protein, whereas SEQ ID NO: 4 represents the short form of the protein lacking the first exon. In addition to the full length FLJ23560 molecule, the present invention also relates to fragments of the polypeptides that may or may not retain various of the functions described below. Fragments, including the N-terminus of the molecule may be generated by genetic engineering of translation stop sites within the coding region (discussed below). Alternatively, treatment of the FLJ23560 with proteolytic enzymes, known as proteases, can produces a variety of N-terminal, C-terminal and internal fragments. Peptides range from 5, 6, 7, 8, 9, 10, 15, 20, 25, 30, 35, 40, 45, and 50 residues, such as those made synthetically, up to 100, 150, 200, 250, 300, 350, 400, 450, 500, 550, 600, 650, 700 and more residues, which are conveniently produced by recombinant means or by proteolytic digestion of full length FLJ23560. Examples of fragments may include contiguous residues of SEQ ID NOs:2 or 4 of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, 300, 400 or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

A. Variants of FLJ23560

Amino acid sequence variants of the FLJ23560 polypeptide can be substitutional, insertional or deletion variants. Deletion variants lack one or more residues of the native protein which are not essential for function or immunogenic activity, and are exemplified by the variants lacking described herein. The variants may be characterized as comprising missense or truncating mutations. Insertional mutants typically involve the addition of material at a non-terminal point in the polypeptide. This may include the insertion of multiple residues or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below.

Amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of FLJ23560, but with altered and even improved therapeutic characteristics.

B. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

C. Purification of Proteins

It will be desirable to purify FLJ23560 or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

D. Antigen Compositions

The present invention also provides for the use of FLJ23560 proteins or peptides as antigens for the immunization of animals relating to the production of antibodies. It is envisioned that FLJ23560 or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

Human FLJ23560 polypeptide, for example, comprising the sequence of SEQ ID NOs:2 or 4 may be used as antigens. The polypeptide may also have one or more of the changes selected from the group consisting of the mutations shown in FIG. 1, 5 or 6. The polypeptide may comprise less than the entire FLJ23560 polypeptide sequence.

E. Antibody Production

In certain embodiments, the present invention provides antibodies that bind with high specificity to the FLJ23560 polypeptides provided herein. Thus, antibodies that bind to the polypeptide of SEQ ID NOs:2 or 4 are provided. In addition to antibodies generated against the full length proteins, antibodies may also be generated in response to smaller constructs comprising epitopic core regions, including wild-type and mutant epitopes. Antibodies that bind to any of the antigens described above are also provided.

Antibodies may bind essentially only to a wild-type BBS10 protein or a disease associated BBS10 protein, e.g., an antibody may bind specifically to an epitope that is present only in a disease associated BBS10, e.g., one listed in the figures, without significant cross-hybridization to a wild-type BBS10 protein. Alternatively, an antibody may bind specifically to an epitope in a wild-type BBS10 protein without significantly binding to a disease associated BBS10 protein. Other antibodies may detect both types of proteins.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. The term "antibody" is used to refer to any antibody-like molecule that has an antigen binding region, and includes antibody fragments such as Fab', Fab, F(ab').sub.2, single domain antibodies (DABs), Fv, scFv (single chain Fv), hybrid antibodies, chimeric antibodies, humanized antibodies and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Humanized" antibodies are also contemplated, as are chimeric antibodies from mouse, rat, or other species, bearing human constant and/or variable region domains, bispecific antibodies, recombinant and engineered antibodies and fragments thereof.

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

F. Antibody Conjugates

The present invention further provides antibodies against FLJ23560, generally of the monoclonal type, that are linked to one or more other agents to form an antibody conjugate. Any antibody of sufficient selectivity, specificity and affinity may be employed as the basis for an antibody conjugate. Such properties may be evaluated using conventional immunological screening methodology known to those of skill in the art.

Certain examples of antibody conjugates are those conjugates in which the antibody is linked to a detectable label. "Detectable labels" are compounds or elements that can be detected due to their specific functional properties, or chemical characteristics, the use of which allows the antibody to which they are attached to be detected, and further quantified if desired. Another such example is the formation of a conjugate comprising an antibody linked to a cytotoxic or anticellular agent, as may be termed "immunotoxins" (described in U.S. Pat. Nos. 5,686,072, 5,578,706, 4,792,447, 5,045,451, 4,664,911 and 5,767,072, each incorporated herein by reference).

Antibody conjugates are thus preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Again, antibody-directed imaging is less preferred for use with this invention.

Many appropriate imaging agents are known in the art, as are methods for their attachment to antibodies (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the antibody (U.S. Pat. No. 4,472,509). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

Antibody conjugates may be used in vivo or in vitro. In vitro the antibody may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

3. Diagnosing BBS and Related Conditions

As discussed above, the present inventors have determined that alterations in the BBS10 gene are associated with BBS and associated diseases or syndromes. Therefore, BBS10 and FLJ23560 may be employed as a diagnostic or prognostic indicator of BBS in general, and of related or associated disorders such as diabetes (diabetes mellitus), hypertension, retinal degeneration (retinopathy), renal carcinoma, renal malformation, congenital heart defects, limb deformity, polydactyly and obesity. Generally, cardiovascular, gastrointestinal, genitourinary, metabolic, neurological, obstetrical, ophthalmological, pediatric, and psychiatric diseases may be predicted. More specifically, point mutations, deletions, insertions or regulatory perturbations relating to BBS10 may be identified. The present invention contemplates further the diagnosis of disease states by detecting changes in the levels of FLJ23560 expression. Diagnosis of BBS may comprise identifying a mutation in BBS10 and may further comprise identifying a mutation in another BBS gene, e.g., BBS 1, 2, 3, 4, 5, 6, 7, 8, 9, 10, 11 or 12.

The methods described herein may be used to determine whether a subject has or is likely to develop BBS or a BBS associated disease, e.g., as described herein. A method may comprise obtaining a biological sample from a subject. A biological sample may be a sample comprising cells, e.g., a tissue sample, a blood sample, a semen sample, hair, or germ cells. It may also be sufficient to obtain a single cell from the subject. A biological sample may also be a cell lysate or an extract of a cell, such as all or a fraction of genomic DNA, RNA (e.g., mRNA) or protein of a subject. A subject may be a human or other animal and may be an adult, a child, a fetus, an embryo or a fertilized cell.

The methods described herein may also be used in counseling of those individuals seeking to have children (e.g., antenatal or prenatal screen). For example, the methods described herein may be used to determine whether a subject has a mutation that is associated with BBS or associated disease, such to, e.g., determine whether any children from the subject are likely to develop the disease. For example, a method may comprise obtaining a sample from a subject and determining the presence of a mutation in BBS10. In other embodiments, the presence of a mutation in BBS10 is investigated in a fertilized egg or embryo. Thus, methods may be used in preimplantation genetic diagnosis, a technique in which doctors can test fertilized eggs for genetic diseases. For example, an egg can be submitted to in vitro fertilization and the presence of a mutation in BBS10 and/or other BBS genes is determined in the fertilized egg (preimplantation), such as by isolating a cell thereof and testing the presence of the mutation in the cell. The fertilized egg can then be implanted into a woman's uterus. Mutations may also be detected in samples obtained by amniocentesis and chorionic villus sampling (CVS). Screening may also be done by non-invasive prenatal diagnosis, such as by screening embryonic blood cells that are found in the mothers blood or fragments of the embryo's DNA that are found in a mother's plasma. Thus, generally, provided herein are methods for determining the presence of one or more mutations in a BBS10 and other BBS nucleic acids or proteins, such as obtained from a cell.

A. Genetic Diagnosis

One embodiment of the instant invention comprises a method for detecting variation in the expression of FLJ23560. This may comprise determining the presence of specific alterations in the expressed product of FLJ23560, or determining the level of expression of the gene.

The biological sample can be any tissue or fluid. Various embodiments include cells of the skin, muscle, fascia, brain, prostate, breast, endometrium, lung, head & neck, pancreas, small intestine, blood cells, liver, testes, ovaries, colon, rectum, skin, stomach, esophagus, spleen, lymph nodes, bone marrow or kidney. Other embodiments include fluid samples such as peripheral blood, lymph fluid, ascites, serous fluid, pleural effusion, sputum, cerebrospinal fluid, lacrimal fluid, stool urine or amniotic fluid.

Nucleic acids used are isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA (cDNA). In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have BBS or BBS-related pathologies. In this way, it is possible to correlate the amount or kind of BBS detected with various clinical states.

Various types of defects have been identified by the present inventors. Thus, "alterations" should be read as including deletions, insertions, point mutations and duplications. Point mutations result in stop codons, frameshift mutations or amino acid substitutions. Somatic mutations are those occurring in non-germline tissues. Germ-line mutation can occur in any tissue and are inherited. Mutations in and outside the coding region also may affect the amount of FLJ23560 produced, both by altering the transcription of the gene or in destabilizing or otherwise altering the processing of either the transcript (mRNA) or protein.

FIGS. 1, 5 and 6 provide a summary of the changes identified in the BBS10 gene, which may be assayed for in a diagnostic assay of the invention. It is contemplated that these and other mutations in the BBS10 gene may be identified as described, e.g., in U.S. Pat. No. 4,988,617. A variety of other assays are also contemplated in this regard, including but not limited to, fluorescent in situ hybridization (FISH; U.S. Pat. No. 5,633,365 and U.S. Pat. No. 5,665,549, each incorporated herein by reference), direct DNA sequencing, PFGE analysis, Southern or Northern blotting, single-stranded conformation analysis (SSCA), RNAse protection assay, allele-specific oligonucleotide (ASO, e.g., U.S. Pat. No. 5,639,611), dot blot analysis, denaturing gradient gel electrophoresis (e.g., U.S. Pat. No. 5,190,856 incorporated herein by reference), RFLP (e.g., U.S. Pat. No. 5,324,631 incorporated herein by reference) and PCR™-SSCP. Methods for detecting and quantitating gene sequences, such as mutated genes and oncogenes, in for example biological fluids are described in U.S. Pat. No. 5,496,699, incorporated herein by reference.

a. Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein) or a chemillumiscent (luciferase).

b. Template Dependent Amplification Methods

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

C. Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

d. Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods (See Sambrook et al., 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

e. Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the NGVN gene that may then be analyzed by direct sequencing.

f. Kit Components

All the essential materials and reagents required for detecting and sequencing BBS10 and variants thereof may be assembled together in a kit. This generally will comprise preselected primers and probes. Also included may be enzymes suitable for amplifying nucleic acids including various polymerases (RT, Taq, Sequenase etc.), deoxynucleotides and buffers to provide the necessary reaction mixture for amplification. Such kits also generally will comprise, in suitable means, distinct containers for each individual reagent and enzyme as well as for each primer or probe.

g. Design and Theoretical Considerations for Relative Quantitative RT-PCR

Reverse transcription (RT) of RNA to cDNA followed by relative quantitative PCR. (RT-PCR) can be used to determine the relative concentrations of specific mRNA species isolated from patients. By determining that the concentration of a specific mRNA species varies, it is shown that the gene encoding the specific mRNA species is differentially expressed.

B. Immunodiagnosis

Antibodies can be used in characterizing the FLJ23560 content of healthy and diseased tissues, through techniques such as ELISAs and Western blotting.

The use of antibodies of the present invention, in an ELISA assay is contemplated. For example, anti-FLJ23560 antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation. Following formation of specific immunocomplexes between the test sample and the bound antibody, and subsequent washing, the occurrence and even amount of immunocomplex formation may be determined by subjecting same to a second antibody having specificity for FLJ23560 that differs the first antibody. Appropriate conditions preferably include diluting the sample with diluents such as BSA, bovine gamma globulin (BGG) and phosphate buffered saline (PBS)/TWEEN. These added agents also tend to assist in the reduction of nonspecific background. Following incubation, the antisera-contacted surface is washed so as to remove non-immunocomplexed material. A preferred washing procedure includes washing with a solution such as PBS/TWEEN, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/TWEEN).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and H2O2, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The steps of various other useful immunodetection methods have been described in the scientific literature, such as, e.g., Nakamura et al., (1987) Immunoassays, in their most simple and direct sense, are binding assays. Certain preferred immunoassays are the various types of radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

5. Methods for Treating BBS

The present invention also contemplates the treatment of BBS and related symptoms such as obesity, diabetes, renal abnormalities, retinal degeneration and hypertension by providing a NGVN protein to cells of an affected individual. A method may comprise administering to a subject in need thereof a therapeutically effective amount of a BBS10 protein or biologically active portion thereof or a nucleic acid encoding such.

A. Genetic Based Therapies

Specifically, the present inventors intend to provide, to a cell, an expression construct capable of providing FLJ23560 to that cell. Because the sequence homology between the human, and other FLJ23560, any of these nucleic acids could be used in human therapy, as could any of the gene sequence variants discussed above which would encode the same, or a biologically equivalent polypeptide. The lengthy discussion of expression vectors and the genetic elements employed therein is incorporated into this section by reference. Particularly preferred expression vectors are viral vectors such as adenovirus, adeno-associated virus, herpesvirus; vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock. Liposomal or other non-viral formulations are also contemplated. Formulation as a pharmaceutically acceptable composition is discussed below.

B. Protein Therapy

Another therapy approach is the provision, to a subject, of FLJ23560 polypeptide, active fragments, synthetic peptides, mimetics or other analogs thereof. The protein may be produced by recombinant expression means. Formulations would be selected based on the route of administration and purpose including, but not limited to, liposomal formulations and classic pharmaceutical preparations.

6. Engineering Expression Constructs

In certain embodiments, the present invention involves the manipulation of genetic material to produce expression constructs that encode a BBS10 gene. Such methods involve the generation of expression constructs containing, for example, a heterologous DNA encoding a gene of interest and a means for its expression, replicating the vector in an appropriate helper cell, obtaining viral particles produced therefrom, and infecting cells with the recombinant virus particles.

The gene will be a wild-type BBS10 gene discussed herein above. In the context of gene therapy, the gene will be a heterologous DNA, meant to include DNA derived from a source other than the viral genome which provides the backbone of the vector. The gene may be derived from a prokaryotic or eukaryotic source such as a bacterium, a virus, a yeast, a parasite, a plant, or even an animal. The heterologous DNA also may be derived from more than one source, i.e., a multigene construct or a fusion protein. The heterologous DNA also may include a regulatory sequence which may be derived from one source and the gene from a different source.

A. Selectable Markers

In certain embodiments of the invention, the therapeutic expression constructs of the present invention contain nucleic acid constructs whose expression may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as herpes simplex virus thymidine kinase (tk) may be employed. Immunologic markers also can be employed. The selectable marker employed is not believed to be important, so long as it is capable of being expressed simultaneously with the nucleic acid encoding a gene product. Further examples of selectable markers are well known to one of skill in the art and include reporters such as EGFP, .beta.-gal or chloramphenicol acetyltransferase (CAT).

B. Control Regions

Throughout this application, the term "expression construct" is meant to include any type of genetic construct containing a nucleic acid coding for gene products in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding genes of interest.

The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Promoters may be composed of discrete functional modules, each consisting of approximately 7-20 bp of DNA, and containing one or more recognition sites for transcriptional activator or repressor proteins.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Several inducible promoter systems are available for production of viral vectors where the transgene product may be toxic.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus. Similarly tissue specific promoters may be used to effect transcription in specific tissues or cells so as to reduce potential toxicity or undesirable effects to non-targeted tissues.

In certain indications, it may be desirable to activate transcription at specific times after administration of the gene therapy vector. This may be done with such promoters as those that are hormone or cytokine regulatable. For example in gene therapy applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful in the present invention. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, L-6 (Poli and Cortese, 1989), Complement C3 (Wilson et al., 1990), IL-8, alpha-1 acid glycoprotein (Prowse and Baumann, 1988), alpha-1 antitypsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin.

It is envisioned that any of the above promoters alone or in combination with another may be useful according to the present invention depending on the action desired. In addition, this list of promoters should not be construed to be exhaustive or limiting, those of skill in the art will know of other promoters that may be used in conjunction with the promoters and methods disclosed herein.

Any promoter/enhancer combination (as per the Eukaryotic Promoter Data Base EPDB) could be used to drive expression of the gene. Eukaryotic cells can support cytoplasmic transcription from certain bacterial promoters if the appropriate bacterial polymerase is provided, either as part of the delivery complex or as an additional genetic expression construct.

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

7. Methods of Gene Transfer

In order to mediate the effect transgene expression in a cell, it will be necessary to transfer the therapeutic expression constructs of the present invention into a cell. Such transfer may employ viral or non-viral methods of gene transfer. This section provides a discussion of methods and compositions of gene transfer.

In certain embodiments, the gene is incorporated into a viral particle to mediate gene transfer to a cell. Typically, the virus simply will be exposed to the appropriate host cell under physiologic conditions, permitting uptake of the virus. The present methods may be advantageously employed using a variety of viral vectors, such as those derived from an adenovirus, a retrovirus, an adeno-associated Virus (AAV), vaccinia virus, canary pox virus, and herpes virus.

Several non-viral methods for the transfer of expression constructs into cultured mammalian cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene therapy.

Liposome-mediated nucleic acid delivery and expression of foreign DNA in vitro has been very successful. Using the beta-lactamase gene, Wong et al., (1980) demonstrated the feasibility of liposome-mediated delivery and expression of foreign DNA in cultured chick embryo, HeLa, and hepatoma cells. Nicolau et al., (1987) accomplished successful liposome-mediated gene transfer in rats after intravenous injection. Also included are various commercial approaches involving "lipofection" technology.

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993). Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al., (1984) successfully injected polyomavirus DNA in the form of $CaPO_4$ precipitates into liver and spleen of adult and newborn mice demonstrating active viral replication and acute infection.

8. Formulations and Routes for Administration to Patients

Where clinical applications are contemplated, it will be necessary to prepare pharmaceutical compositions—expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The present description is further illustrated by the following examples, which should not be construed as limiting in any way. The contents of all cited references (including literature references, issued patents, published patent applications and GenBank Accession numbers as cited throughout this application) are hereby expressly incorporated by reference. When definitions of terms in documents that are incorporated by reference herein conflict with those used herein, the definitions used herein govern.

EXAMPLES

To identify novel BBS genes, we performed a genome-wide scan in a large, consanguineous pedigree of Lebanese origin. SNP-based mapping identified two regions of homozygosity that segregated with the disease phenotype in different sibships. One region encompassed the BBS2 locus, while the other spanned 8 Mb of homozygosity for three sibships on chromosome 12q and contained 23 annotated genes (Laurier et al, in preparation). In one of these transcripts, the putative chaperonin FLJ23560, we found in the affected subjects a homozygous missense serine to alanine (S311A) change that was not present in 107 Lebanese and 50 European controls. Analysis of this gene in a few multiplex or consanguineous families in which linkage analysis was compatible with a chromosome 12 locus revealed several truncating mutations, indicating that FLJ23560 represents indeed a novel BBS locus, BBS10. To fully explore the involvement of this gene in BBS, we sequenced 311 families, without preselection against families with known BBS mutations. We found likely pathogenic changes in ~21% of families (n=65; FIG. 5) and a number of seemingly benign variants (FIG. 6), rendering BBS10 a novel and major BBS gene, mutated as frequently as BBS1. Notably, we found a similar frequency of mutations in families of Middle Eastern ancestry (6/26) in contrast to the minimal contribution of the other BBS loci (3-10%), including BBS1.

Figure 1B:
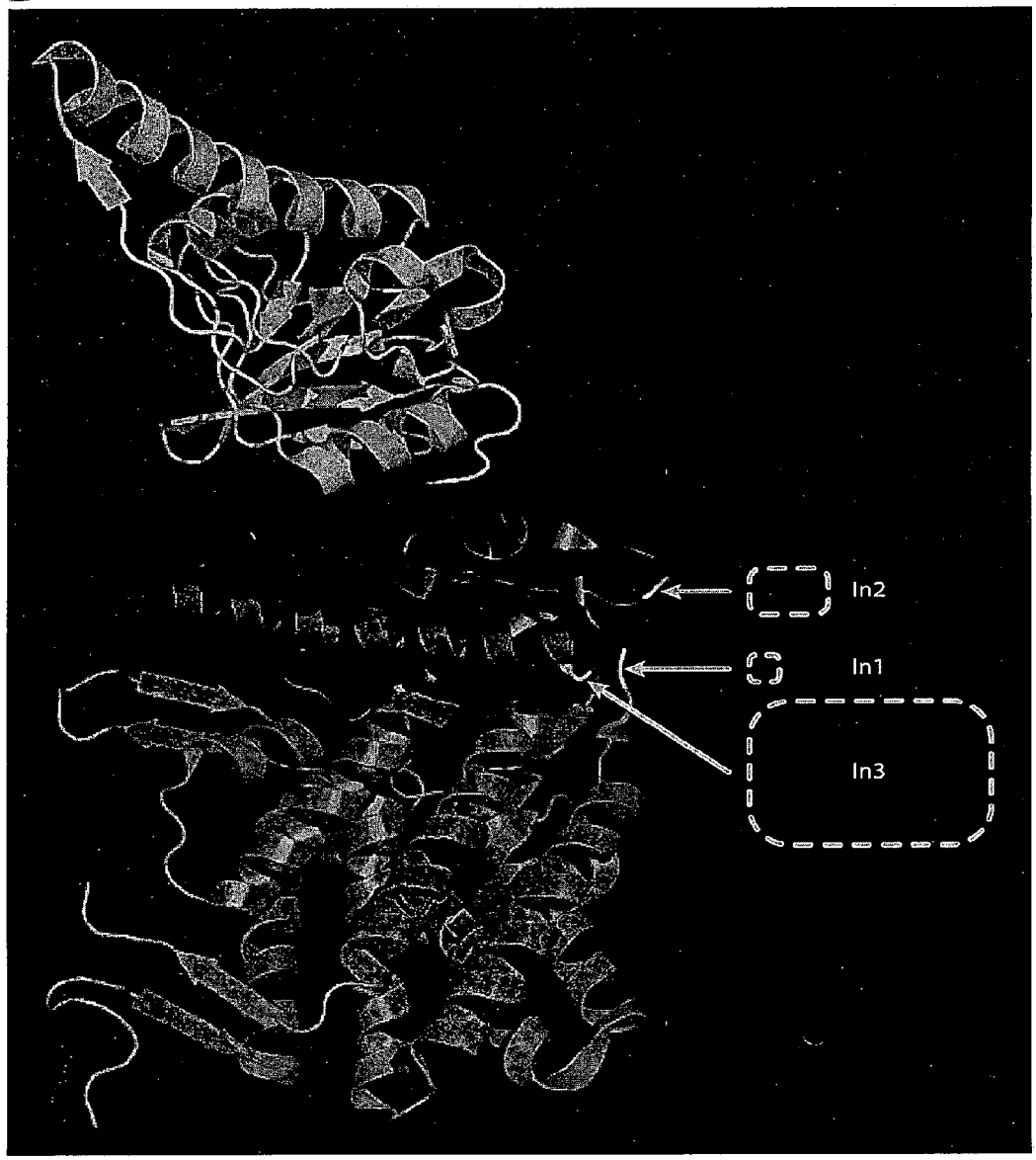
Figure 7:
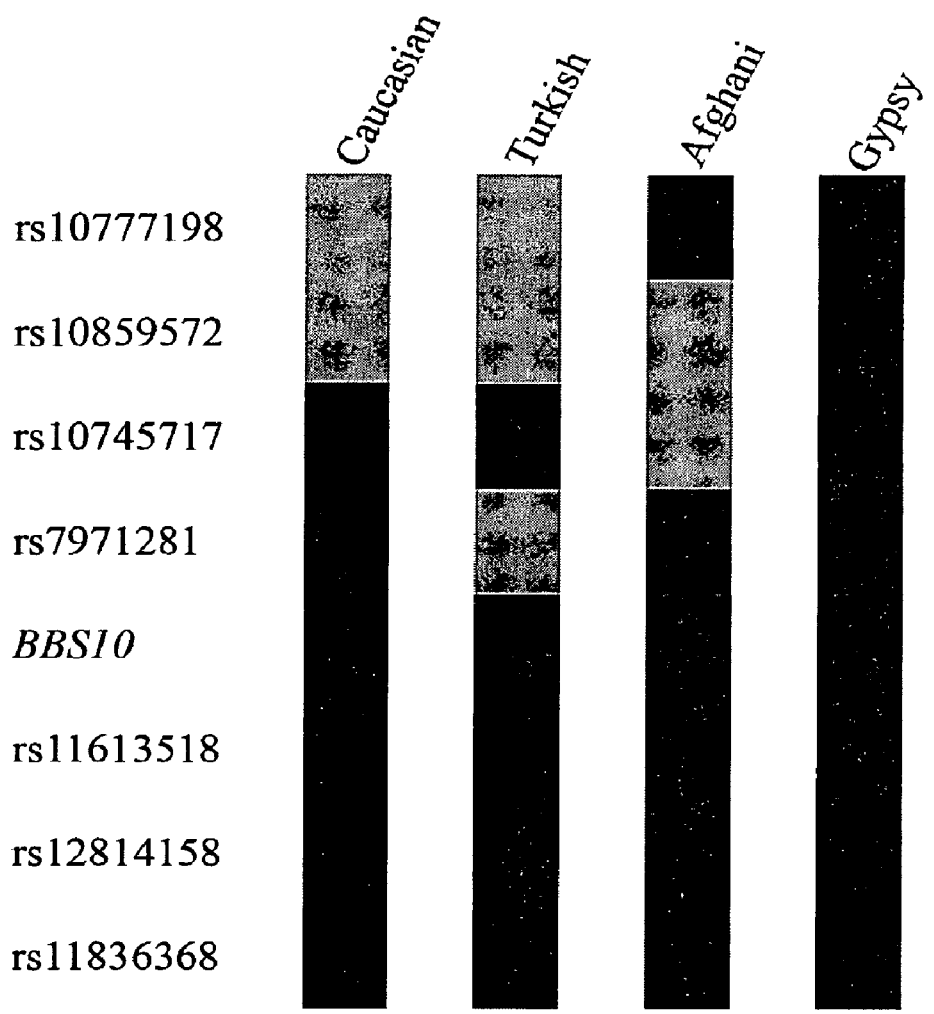
FIG. 7 shows C91 fsX95 is an ancient mutation encompassed by a conserved haplotype block. Genotyping of SNPs flanking BBS 10 in individuals homozygous for the C91 fs variant (See FIG. 5) place the mutation within a continuous haplotype which extends >175 kb distally from BBS10 in all ethnicities. Vertical bars depict the BBS10 chromosomal region sorted by ethnicity with red and gray representing shared and unshared haplotypes respectively. Confirmed HapMap SNPs rs10777198, rs10859572, rs10745717, rs7971281, rs11613518, rs12814158, and rs11836368 are located −84263 bp, −44261 bp, −31372 bp, −13703 bp, 18519 bp, 146940 bp, and 175125 bp respectively from BBS10.

We found a total of 118 mutant alleles, among which 53 families segregated two mutations consonant with the clinical phenotype; in 12 families, we found only a single, heterozygous mutation, which either might reflect the presence of a second mutation in a regulatory region of BBS10 or might result from oligogenic inheritance. A single base insertion at amino acid 91, leading to premature termination four codons later (C91fsX95), accounted for 54 mutant alleles (46%). Although this allele is most frequent in Caucasians, reminiscent of the prevalence of the M390R mutation in BBS1[4], we also found it in families of Turkish and Afghani origin, suggesting that it may represent either an ancient allele or a site of recurrent mutations. SNP-based haplotype analysis across a ~230 kb region centered on BBS10 showed the former to be the likely case, since we detected a common haplotype on the C91fsX95-bearing chromosome extending at least 175 kb distally in all ethnic groups in our cohort (Suppl. FIG. 1). Most truncating mutations (15/16) are also frameshifts, and we detected 16 different missense mutations spreading from Nter (R34P) to Cter (T689P and also a distal V707 frameshift) (FIG. 1a). None of the mutant alleles shown in Suppl. Table 1 was present in 96 controls screened by DNA sequencing.

We next queried whether BBS10 participates in complex Mendelian inheritance. We found no unaffected sibs or parents who had homozygous or compound heterozygous mutations for BBS10, suggesting that two BBS10 mutations are sufficient for pathogenesis of the phenotype. However, 12/65 families (18%) also had mutations or recognized variants at another BBS locus, indicative of a potential epistatic interaction (FIG. 5). Most of these mutations were missense variants and thus the possibility that they are benign cannot be excluded. Three families provided more compelling evidence. Two families with two BBS10 mutations have one additional pathogenic BBS1 mutation (M390R or a splice junction mutation IVS13-2A→G). A third family with a single BBS10 mutation (S303fsX305) carries two bona fide BBS1 mutations (M390R/E549X).

Extensive database searches and sequence analyses revealed several BBS10 homologues and clearly relate BBS10 to the group II chaperonins. In sharp contrast to all known BBS proteins, including BBS6, another putative chaperonin[10], BBS10 is restricted to vertebrates. Within vertebrates, BBS10 is the fastest evolving (or least evolutionary constrained) of BBS genes (FIG. 8). The chaperonin domain organization is conserved in BBS10, encompassing the three major functional domains: equatorial, intermediate, and apical (FIGS. 1a,b), and the flexible protrusion region specific to group II chaperonins[11]. The functional motif GDGTT[T/S], responsible for ATP hydrolysis in all group II chaperonins[11], is conserved in BBS10 homologues (GDG[A/V/S/T]K[T/S]). This suggests that BBS10 may be an active enzyme in contrast to BBS6, in which the catalytic site is missing[10].

Compared to both the prototypic group II chaperonin and BBS6 sequences, the BBS10 family contains three specific insertions in the intermediate domain: two small insertions noted In1 (8 amino acids at position 129), In2 (29 amino acids at position 187) and one large insertion, In3 (ranging from 19 to 170 amino acids at position 426; FIG. 1a). At the structural level (FIG. 1b), the three insertions protrude in remarkable spatial closeness on the same face of the intermediate domain, suggesting that they may cooperate to define an additional domain. Given the structural constraints introduced by this additional domain, BBS10 is unlikely to assemble in the prototypic chaperonin multisubunit complex[10,11]. This observation, together with the distinct phylogeny of BBS10 indicates that this protein defines a novel chaperonin subfamily (FIG. c).

To explore the function of this molecule further and to assay its genetic interaction with other BBS proteins, we modeled loss of BBS10 function in zebrafish. Computational analysis of the zebrafish genome with the human sequence identified a single ortholog. Upon confirmation by RT-PCR (data not shown), we designed two non-overlapping translational morpholinos (MOs). Injection of serial MO concentrations into wild-type embryos yielded dosage-dependent early developmental defects in gastrulation movements that are consistent both with morphant phenotypes for other bbs genes[12] and the recently-developed hypothesis implicating the BBS proteins in the Planar Cell Polarity pathway[7]. Although the phenotype was generally mild (and reminiscent of the only other BBS-associated chaperonin-like, BBS6[12]), suppression of maternal bbs10 message caused shortening of the rostrocaudal body axis and dorsal thinning, broadening and kinking of the notochord, elongation of the somites, and decreased somitic definition and symmetry (FIG. 2a). The phenotype was specific since it could be both recapitulated with a second bbs10 MO and rescued by co-injecting bbs10 mRNA. These observations also enabled us to test for genetic interaction with other bbs genes by injecting sub-effective MO doses for each transcript and by assaying for synthetic and/or exacerbated phenotypes. Co-injection of bbs1/bbs10 and bbs6/bbs10 MOs had a modest, but appreciable effect of the phenotype. In each case, the addition of a second morpholino caused a modest increase on the overall proportion of affected embryos and a notable expansion of the Class II (severe) phenotype, suggesting that the presence of a second MO had a primarily modifying effect on the expressivity of the phenotype (FIG. 2b). The interaction was most pronounced between bbs4 and bbs10, where more than 50% of co-injected embryos exhibited somitic and notochordal defects (FIG. 2b), and detachment of cells along the entire rostrocaudal axis, a phenotype found only in very high dosage bbs4 morphants and never in the administered bbs4 MO dosage (n>400 embryos)[12].

The identification of BBS10 as a major locus for BBS across ethnic groups will have profound diagnostic consequences and warrants detailed phenotype-genotype correlation studies. In addition, that BBS10 appears to be a bona fide chaperonin, unlike BBS6, which has lost its ATP-binding site, potentially provides a new angle on the functional dissection of BBS. It will be important to place BBS10 in the formation and function of basal body and primary cilia and to determine whether it controls folding or stability of other ciliary or basal body proteins. BBS10 is vertebrate-specific and would thus have been missed by the comparative genomics approaches used recently to find BBS genes by their conservation in ciliated organisms[2,13,14,15].

REFERENCES

1. Beales, P. *Curr Opin Genet Dev.* 15, 315-23 (2005).
2. Nishimura, D. Y. et al. *Am J Hum Genet*. In press
3. Hichri, H. et al. *Eur J Hum Genet.* 13, 607-616 (2005).
4. Katsanis, N. *Hum Mol Genet.* 1; 13 (2004).
5. Katsanis, N. et al. *Science* 293:2256-9 (2001).
6. Ansley, S. J. et al. *Nature* 425:628-33 (2003).
7. Ross, A. J. et al. *Nat Genet.* 37:1135-40 (2005).
8. Blacque, O. et al. *Genes Dev.* 18:1630-1642 (2004).
9. Kulaga, H. M. et al. *Nat Genet.* 36:994-8 (2004).
10. Kim, J. C. et al. *J Cell Sci.* 118:1007-1020 (2005).
11. Ditzel, L. et al. *Cell* 93:125-38 (1998).
12. Badano, J. L. et al. *Nature* (December 2005)
13. Fan, Y. et al. *Nature Genet.* 36: 989-993 (2004).
14. Chiang, A. P. et al. *Am J Hum Genet.* 75:475-484 (2004).
15. Li, J. B. et al. *Cell* 117:541-52 (2004).

Materials and Methods

BBS Patients and Mutational Analyses.

We performed PCR from DNA extracted from lymphoblastoid cell lines or from lymphocytes according to standard protocols. PCR products were purified with the Exo-SAP cleanup kit (USB) and sequenced with dye-primer or dye-terminator chemistry and ABI 3100 or 377 (Applied Bio systems) or MegaBACE1000 (Amersham) automated sequencer. Primer sequences and BBS10 amplification conditions are set forth below. Mutated BBS10 alleles were absent from at least 192 control DNAs.

|  | Forward Reverse | size | PCR Conditions |
|---|---|---|---|
| Exon 1 | GAAGCCGTGCTACCCCGGCT (SEQ ID NO: 5) CGCATCGCCTCAGGATGGGA (SEQ ID NO: 6) | 417 bp | TD -> 67° C. -60° C. 2 mM MgCl$_2$ |
| Exon 2 amplicon 1 | GATGTGGGAAGCCAGCCTTC (SEQ ID NO: 7) GGCCAGTGACACCAACATTC (SEQ ID NO: 8) | 539 bp | 58° C. 1.5 mM MgCl$_2$ |
| Exon 2 amplicon 2 | CACAGTTGATGTGTGACTAC (SEQ ID NO: 9) | 535 bp | 58° C. 1.5 mM MgCl$_2$ |

-continued

| | Forward Reverse | size | PCR Conditions |
|---|---|---|---|
| | TTCACCAAAGCAGTGTTAGG (SEQ ID NO: 10) | | |
| Exon 2 amplicon 3 | TCCGGAGGATCATTGGTCTT (SEQ ID NO: 11) CATGTCAGCGTTTCAACTGT (SEQ ID NO: 12) | 551 bp | 58° C. 1.5 mM MgCl$_2$ |
| Exon 2 amplicon 4 | CAGGACACAGTTGCAGAGAA (SEQ ID NO: 13) GCAGTGCATGGACAGCTCTT (SEQ ID NO: 14) | 589 bp | 58° C. 1.5 mM MgCl$_2$ |
| Exon 2 amplicon 5 | CCTCATCTATGCCAGCTGGT (SEQ ID NO: 15) ACCAGTGGTCACATGACTGC (SEQ ID NO: 16) | 473 bp | 58° C. 1.5 mM MgCl$_2$ |

Yet Other Primers and PCR Conditions are Provided Below:
PCR Primers:

| BBS10 x 1Fwd | TGTAAAACGACGGCCAGTGGTTTTCTCCCCGCCTATT (SEQ ID NO: 17) |
|---|---|
| BBS10 x 1Rev | CAGGAAACAGCTATGACCTCACCCGAGGTCAGTCTTTC (SEQ ID NO: 18) |
| BBS10 x 2A Fwd | TGTAAAACGACGGCCAGTGATGTATCCAAGGAACAATATTCTCA (SEQ ID NO: 19) |
| BBS10 x 2A Rev | CAGGAAACAGCTATGACCTTTCTTCCCACTCTTCCACAA (SEQ ID NO: 20) |
| BBS10 x 2B Fwd | TGTAAAACGACGGCCAGTGACGGTATTATGGACCAGTACC (SEQ ID NO: 21) |
| BBS10 x 2B Rev | CAGGAAACAGCTATGACCTGAGCAATTTTACATTCTGACTATG (SEQ ID NO: 22) |
| BBS10 x 2C Fwd | TGTAAAACGACGGCCAGTCAGAAACCATTCAGCCTCTTTT (SEQ ID NO: 23) |
| BBS10 x 2C Rev | CAGGAAACAGCTATGACCGGTCTTTAAATAATTGCCGAAGC (SEQ ID NO: 24) |
| BBS10 x 2D Fwd | TGTAAAACGACGGCCAGTTCCAAAAGATATGTTCATCTAGGC (SEQ ID NO: 25) |
| BBS10 x 2D Rev | CAGGAAACAGCTATGACCAAGCAGTGGAATTGTTCTTGAG (SEQ ID NO: 26) |
| BBS11 x 2E FwdN | TGTAAAACGACGGCCAGTCCAAACAGTTGAAACGCTGA (SEQ ID NO: 27) |
| BBS11 x 2E RevN | CAGGAAACAGCTATGACCATTGGTTTGCAGTGCATGG (SEQ ID NO: 28) |
| BBS11 x 2F FwdN | TGTAAAACGACGGCCAGTTTTAGGCATTCCCAAAGTCC (SEQ ID NO: 29) |
| BBS11 x 2F RevN | CAGGAAACAGCTATGACCGGTCTGGTGACCTTAGTGTGC (SEQ ID NO: 30) |

PCR Reaction:
Exon 1
Exon 2A
Exon 2D
Exon 2EN
PCR-96 Well Plate Format:

| | [initial] | [1 rxn final] | 1 Plate (µl) |
|---|---|---|---|
| Buffer* | 10X | 1X | 300 |
| Primer Fwd | 100 µM | 125 nM | 3.6 |
| Primer Rev | 100 µM | 125 nM | 3.6 |
| dNTPs | 2 mM | 200 µM | 300 |
| Taq | 5 U/µl | | 13 |
| H$_2$O | | | 2250 |
| Genomic DNA | 30 ng/µl | 30 ng | 1 |
| Total Volume | | | 25 |

*10X Buffer contains 15 mM Mg$^{2+}$

PCR Reaction:
Exon 2B
Exon 2C
Exon 2FN
PCR-96 Well Plate Format:

| | [initial] | [1 rxn final] | 1 Plate (µl) |
|---|---|---|---|
| Buffer** | 2X | 1X | 1435 |
| Primer Fwd | 100 µM | 125 nM | 3.6 |
| Primer Rev | 100 µM | 125 nM | 3.6 |
| Taq | 5 U/µl | | 13 |
| H$_2$O | | | 1415 |
| Genomic DNA | 30 ng/µl | 30 ng | 1 |
| Total Volume | | | 25 |

**2X FailSafe PCR Buffer PreMix B (Epicentre Biotechnologies Cat. No. FSP995B)

PCR Program (for all Primer Pairs):

| TOUCHDOWN1 | 95° | 5 min | 1X |
|---|---|---|---|
| | 95° | 30 sec | 10X |

-continued

| | | | |
|---|---|---|---|
| 64° (−1°/cycle) | 30 sec | | |
| 72° | 30 sec | | |
| 95° | 30 sec | 35X | |
| 54° | 30 sec | | |
| 72° | 30 sec | | |
| 72° | 10 min | 1X | |
| 4° | ∞ | | |

Bioinformatics.

A PSI-BLAST[1] exploration in Uniprot[2] was performed and the sequences detected with E<10$^{-3}$ were aligned using the PipeAlign program available at http://bips.u-strasbg.fr/PipeAlign[3]. The multiple alignment was manually adjusted, paying attention to secondary structures leading to 280 sequences corresponding to α, β, γ, δ, ε, ζ, η and θ CCT chaperonin subunits, archeal chaperonins, BBS6 and BBS10 sequences.

Phylogenetic Tree.

A phylogenetic tree was built with Phylo_win[4] using representative sequences from each different chaperonin subunit, BBS10 and BBS6. The parameters where set to global gap removal using the neighbor joining method. Branches were tested by bootstrapping (500 replicates) and the tree was edited and displayed with TreeView (http://taxonomy.zoology.gla.ac.uk/rod/treeview.html). The multiple alignment used for phylogenetic analyses contains 211 positions between the selected sequences.

Phylogenetic Distribution of BBS10 in Complete Genomes.

Phylogenetic distribution of BBS10 was examined in 26 eukaryotic organisms for which the genome sequences are available. The presence/absence of each BBS10 was cross validated at both the proteomic and genomic levels. Where available, the genomic sequences were directly queried using ensembl genome browser (http://www.ensembl.org) or by TBLASTN program within the NCBI nucleotide sequence database known as GenBank[5] and RefSeq[6]. The 26 eukaryotic genomes used are: *Thalassiosira pseudonana, Cryptosporidium parvum, Cyanidioschyzon merolae, Oryza sativa, Arabidopsis thaliana, Dictyostelium discoideum, Plasmodium falciparum, Encephalitozoon cuniculi, Neurospora crassa, Saccharomyces cerevisiae, Candida glabrata, Yarrowia lipolytica, Schyzosaccharomyces pombe, Anopheles gambiae, Drosophila melanogaster, C. elegans, Ciona intestinalis, T. nigroviridis, T. rubripes, D. rerio, G. gallus, R. norvegicus, M musculus, B. taurus, C. familiaris* and *H. sapiens*.

The putative BBS10 sequences were also created for the 6 following vertebrate genomes; *B. Taurus, G. gallus, C. familiaris, R. norvegicus, D. rerio* and *T. rubripes*.

Comparative Sequence Analysis of all Known BBS Gene.

When available, the BBS1-9 proteins sequences from *H. sapiens* to *C. elegans* were retrieved from protein databases and aligned using the same protocol as for BBS10. Sequence identities and similarities were computed for each of the BBS1-10 family as the pairwise percent identity (or similarity) of each sequence against the human protein sequence. Positions in the alignment of these sequences corresponding to gaps were excluded from the calculation.

Morpholinos and Embryo Manipulations.

Translational blocking morpholinos designed by Gene Tools Inc were diluted to the appropriate concentrations in deionized, sterile water and injected into 2-cell stage embryos as described[12]. To rescue the morphant phenotypes, we amplified the open reading frame of bbs10 and cloned it into the pCS2+ vector, from which RNA was transcribed in vitro with the SP6 mMessage mMachine kit (Ambion). The classification of morphant embryos into two graded phenotypes was based on previously established criteria[12].

REFERENCES FOR SUPPLEMENTARY METHODS

1. Altschul, S. F. et al. Gapped BLAST and PSI-BLAST: a new generation of protein database search programs. *Nucleic Acids Res* 25, 3389-402 (1997).
2. Bairoch, A. et al. The Universal Protein Resource (UniProt). *Nucleic Acids Res* 33 Database Issue, D154-9 (2005).
3. Plewniak, F. et al. PipeAlign: A new toolkit for protein family analysis. *Nucleic Acids Res* 31, 3829-32 (2003).
4. Galtier, N., Gouy, M. & Gautier, C. SEAVIEW and PHYLO_WIN: two graphic tools for sequence alignment and molecular phylogeny. *Comput Appl Biosci* 12, 543-8 (1996).
5. Benson, D. A., Karsch-Mizrachi, I., Lipman, D. J., Ostell, J. & Wheeler, D. L. GenBank. *Nucleic Acids Res* 33 Database Issue, D34-8 (2005).
6. Pruitt, K. D., Tatusova, T. & Maglott, D. R. NCBI Reference Sequence (RefSeq): a curated non-redundant sequence database of genomes, transcripts and proteins. *Nucleic Acids Res* 33 Database Issue, D501-4 (2005).

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method for determining whether a subject has or is likely to develop Bardet-Biedl Syndrome (BBS), comprising the steps of:
providing a biological sample of a subject; and
determining whether the sample comprises a nucleotide sequence encoding a variant BBS10 polypeptide sequence, wherein the variant BBS10 polypeptide sequence has an amino acid sequence that differs from the sequence set forth in SEQ ID NO: 2 by one or more mutations selected from the group consisting of R34P, R49W, C91W, L170S, C195W, Y197C, F199Del, V240G, L308F, S311A, S329L, P363L, L414S, K579R, Y613H, Y613C, G677V, T689P, A13fs, S73fs, C91fs, V230fs, Q242fs, K243fs, F275fs, S303fs, Y321X, L348fs, L367fs, A474fs, T483fs, T514fs, Y559fs, and V707fs
wherein the presence of a nucleotide sequence that encodes the variant BBS10 polypeptide sequence indicates that the subject has or is likely to develop BBS.

2. The method of claim 1, further comprising: determining whether the sample comprises a second nucleotide sequence encoding second variant BBS10 polypeptide sequence, wherein the second variant BBS10 polypeptide sequence has an amino acid sequence that differs from the sequence set forth in SEQ ID NO: 2 by one or more mutations selected from the group consisting of R34P, R49W, C91W, L170S, C195W, Y197C, F199Del, V240G, L308F, S311A, S329L, P363L, L414S, K579R, Y613H, Y613C, G677V, T689P, A13fs, S73fs, C91fs, V230fs, Q242fs, K243fs, F275fs, S303fs, Y321X, L348fs, L367fs, A474fs, T483fs, T514fs, Y559fs, and V707fs.

3. The method of claim 1, wherein the biological sample is a sample selected from the group consisting of a tissue sample, a blood sample, a semen sample and a germ cell sample.

4. The method of claim 1, wherein the subject is a human adult, a human child, a human fetus, a human embryo or a human fertilized cell.

5. The method of claim 1, wherein the determining step is performed by sequencing the BBS10 nucleic acid.

6. The method of claim 1, wherein the determining step is performed by hybridizing a nucleic acid probe to the BBS10 nucleic acid or an amplification product thereof.

* * * * *

UNITED STATES PATENT AND TRADEMARK OFFICE
CERTIFICATE OF CORRECTION

PATENT NO. : 8,163,482 B2  
APPLICATION NO. : 12/280498  
DATED : April 24, 2012  
INVENTOR(S) : Nicholas Katsanis et al.

Page 1 of 1

It is certified that error appears in the above-identified patent and that said Letters Patent is hereby corrected as shown below:

On the Title page, Item (73), Assignee, insert:

--The Johns Hopkins University, Baltimore, MD (US)  
UCL Business PLC, London, UK (GB)  
Universite de Strasbourg, Strasbourge Cedex, FR (FR)  
Baylor College of Medicine, Houston, TX (US)--

Signed and Sealed this
Fifteenth Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,163,482 B2
APPLICATION NO. : 12/280498
DATED : April 24, 2012
INVENTOR(S) : Nicholas Katsanis et al.

It is certified that error appears in the above-identified patent and that said Letters Patent is hereby corrected as shown below:

On the Title page,

Below Item (54), delete "(76)" and insert --(75)--

Item (73), Assignee, insert:

--The Johns Hopkins University, Baltimore, MD (US)
UCL Business PLC, London, UK (GB)
Universite de Strasbourg, Strasbourge Cedex, FR (FR)
Baylor College of Medicine, Houston, TX (US)--

This certificate supersedes the Certificate of Correction issued April 15, 2014.

Signed and Sealed this
Twenty-second Day of November, 2016

Michelle K. Lee
*Director of the United States Patent and Trademark Office*